US011485979B2

United States Patent
Ito et al.

(10) Patent No.: US 11,485,979 B2
(45) Date of Patent: Nov. 1, 2022

(54) CELL AND METHOD FOR PRODUCING TARGET PROTEIN USING SAME

(71) Applicants: NATIONAL UNIVERSITY CORPORATION KOBE UNIVERSITY, Hyogo (JP); KANEKA CORPORATION, Osaka (JP)

(72) Inventors: Yoichiro Ito, Hyogo (JP); Jun Ishii, Hyogo (JP); Yasuyuki Nakamura, Hyogo (JP); Akihiko Kondo, Hyogo (JP); Teruyuki Nishi, Hyogo (JP)

(73) Assignees: NATIONAL UNIVERSITY CORPORATION KOBE UNIVERSITY, Hyogo (JP); KANEKA CORPORATION, Osaka (JP)

( * ) Notice: Subject to any disclaimer, the term of this patent is extended or adjusted under 35 U.S.C. 154(b) by 0 days.

(21) Appl. No.: 17/032,943

(22) Filed: Sep. 25, 2020

(65) Prior Publication Data

US 2021/0017528 A1 Jan. 21, 2021

Related U.S. Application Data

(63) Continuation of application No. PCT/JP2019/007434, filed on Feb. 27, 2019.

(30) Foreign Application Priority Data

Mar. 26, 2018 (JP) .............................. JP2018-058953

(51) Int. Cl.
*C12N 15/81* (2006.01)
*C12N 5/10* (2006.01)
*C12P 21/00* (2006.01)

(52) U.S. Cl.
CPC ............... *C12N 15/81* (2013.01); *C12N 5/10* (2013.01); *C12P 21/00* (2013.01)

(58) Field of Classification Search
CPC ........ C12N 15/81; C12N 5/10; C12N 15/815; C12P 21/00; C12P 21/02
See application file for complete search history.

(56) References Cited

U.S. PATENT DOCUMENTS

2019/0010194 A1 1/2019 Nishi

FOREIGN PATENT DOCUMENTS

| EP | 2669375 A1 | 12/2013 |
| JP | 2016-146789 A | 8/2016 |
| JP | 2018-38286 A | 3/2018 |
| WO | 2012/102171 A1 | 8/2012 |
| WO | 2017/137579 A1 | 8/2017 |
| WO | 2017/170468 A1 | 10/2017 |

OTHER PUBLICATIONS

M. Ahmad et al., "Protein expression in Pichia pastoris: recent achievements and perspectives for heterologous protein production", Appl Microbiol Biotechnol, 2014, vol. 98, pp. 5301-5317 (17 pages).
Y. Liu et al., "Expression of single-domain antibody in different systems", Appl Microbiol Biotechnol, 2018, vol. 102, pp. 539-551 (13 pages).
Database GenBank [online], Accession No. CCA37552 (2 pages).
International Search Report issued in International Application No. PCT/JP2019/007434, dated Jun. 4, 2019 (1 page).
Written Opinion issued in International Application No. PCT/JP2019/007434, dated Jun. 4, 2019 (4 pages).
Extended European Search Report issued in corresponding EP Application No. 19774453.5 dated Nov. 18, 2021 (7 pages).
Kristof De Schutter et al., "Genome Sequence of the recombinant protein production host Pichia pastoris" Nature Biotechnology, vol. 27, No. 6, Jun. 1, 2009, pp. 561-566 (9 pages).

*Primary Examiner* — Paul J Holland
(74) *Attorney, Agent, or Firm* — Osha Bergman Watanabe & Burton LLP

(57) ABSTRACT

One or more embodiments of the present invention are to provide a new means of improving the productivity of a target protein. The present inventors have identified a novel protein consisting of the amino acid sequence set forth in SEQ ID NO: 2 through an exhaustive analysis of the nucleotide sequence of chromosomal DNA of a yeast belonging to the genus *Komagataella*. Activation of a gene encoding the novel protein provides a cell having an improved productivity of a target protein.

8 Claims, No Drawings

Specification includes a Sequence Listing.

SEQUENCE LISTING

```
<160> NUMBER OF SEQ ID NOS: 42

<210> SEQ ID NO 1
<211> LENGTH: 1650
<212> TYPE: DNA
<213> ORGANISM: Komagataella pastoris

<400> SEQUENCE: 1
atgtcagtcg ttccgtacca aaaggaccta agggtggttt ggaagcatcc tgattccaga      60
tccgtagttc tctactccaa agagcatcag agcttccagt atatttcttt agacagagtt     120
gatgaagtca atggatcaga tagtgactat tttcacagta aaaacggaag taaccaacga     180
agaagatcat cgacagtatg tccgagatgt ggctttaata tgagtagatc atctccagaa     240
tccatgttca ataacaacta cttcaagctg cttgcaaacg ttcaaagcaa taaactatca     300
gagcaagaaa aagatagcca tatgaatttg ctcaatagcg ccataaagtt cccatccttt     360
aaattgaacc gatccacttt tccggacaat ctattcagtc agggctattt tgcaaagttc     420
ttcacagaat taaatgtttt ggggcatggt agtaacgggg tggtgctcaa agttgaacat     480
gtattgaatg attcatgtct cggggtattt gctctgaaga aaattagtat tggagagaag     540
ctctccaacc ttgaaaatgt tctcaacgag gtcaagatat tataccagtt aaccaacgca     600
gatgtgcaat taggaggcaa cctggttagt tataatcatg tctggctgga agttgatcaa     660
ccgactgatt tcggcccaaa ggtcccttgt gtgttcatct tatttgaata ctgtgatgga     720
ggagatttgg aaagcttcat tgatcggctt aaacaccca agctcgacat agaacaggag     780
aaacaatata gaaggatggt aagaaaggga ctaactgcag aaagaggagt acacgagcct     840
cggtctctta acgacgtgga gatttggaaa ctgttcaaag atattacaaa tggtgttcaa     900
caattgcatt cttctcatat attacacaga gacttaaagc catctaattg tctattaaaa     960
tacaggtatg aaaaggaggt cacccagttg gatgagtata atgacattcc aaaagtcatg    1020
gtgagtgatt ttggagaggg aactttttgac aatatcgaac gttcctcgtc aggatacacc    1080
ggaaccttag agttcaccgc tccagaagtg tttggctcga actattcacg agctagtgat    1140
gtttattctc taggattgat cttatatttc ttgtgtttcg gtgaccttcc gtataaaaca    1200
caggatataa aaagagaaat tcaacaatac gctaaggag atcggacct ctttacagaa    1260 attgatgtta ttaggaacga tatctccaaa gattgggtca aactgattct tgaatgttgc    1320
tctttagacg cagataaacg gccttcagcc tcagaaatct tggcaaattt gaatactatt    1380
tacttgcaat tggaagccaa acaacaaaat aaagaacatc ctgagccaga agcatacggt    1440
atccaccctc ctgattcgtt caactatcca aaatttcttg cagtgattgt aaatgtgtta    1500
ctactgaagg ttcaacaaaa cacattcaaa atggtaacat gtttcatcat tggcctatca    1560
tttcacgtta caaccaaaaa catgatcatg ctaagtgtgt tgaatgcgct ttttcggtg    1620 ctttcgattg tctatcttaa cagcaactag                                     1650

<210> SEQ ID NO 2
<211> LENGTH: 549
<212> TYPE: PRT
<213> ORGANISM: Komagataella pastoris
```

<400> SEQUENCE: 2

```
Met Ser Val Val Pro Tyr Gln Lys Asp Leu Arg Val Val Trp Lys His
1               5                   10                  15

Pro Asp Ser Arg Ser Val Val Leu Tyr Ser Lys Glu His Gln Ser Phe
            20                  25                  30

Gln Tyr Ile Ser Leu Asp Arg Val Asp Glu Val Asn Gly Ser Asp Ser
        35                  40                  45

Asp Tyr Phe His Ser Lys Asn Gly Ser Asn Gln Arg Arg Arg Ser Ser
    50                  55                  60

Thr Val Cys Pro Arg Cys Gly Phe Asn Met Ser Arg Ser Ser Pro Glu
65                  70                  75                  80

Ser Met Phe Asn Asn Asn Tyr Phe Lys Leu Leu Ala Asn Val Gln Ser
                85                  90                  95

Asn Lys Leu Ser Glu Gln Glu Lys Asp Ser His Met Asn Leu Leu Asn
            100                 105                 110

Ser Ala Ile Lys Phe Pro Ser Phe Lys Leu Asn Arg Ser Thr Phe Pro
        115                 120                 125

Asp Asn Leu Phe Ser Gln Gly Tyr Phe Ala Lys Phe Phe Thr Glu Leu
    130                 135                 140

Asn Val Leu Gly His Gly Ser Asn Gly Val Val Leu Lys Val Glu His
145                 150                 155                 160

Val Leu Asn Asp Ser Cys Leu Gly Val Phe Ala Leu Lys Lys Ile Ser
                165                 170                 175

Ile Gly Glu Lys Leu Ser Asn Leu Glu Asn Val Leu Asn Glu Val Lys
            180                 185                 190

Ile Leu Tyr Gln Leu Thr Asn Ala Asp Val Gln Leu Gly Gly Asn Leu
        195                 200                 205

Val Ser Tyr Asn His Val Trp Leu Glu Val Asp Gln Pro Thr Asp Phe
    210                 215                 220

Gly Pro Lys Val Pro Cys Val Phe Ile Leu Phe Glu Tyr Cys Asp Gly
225                 230                 235                 240

Gly Asp Leu Glu Ser Phe Ile Asp Arg Leu Lys His Pro Lys Leu Asp
                245                 250                 255

Ile Glu Gln Glu Lys Gln Tyr Arg Arg Met Val Arg Lys Gly Leu Thr
            260                 265                 270

Ala Glu Arg Gly Val His Glu Pro Arg Ser Leu Asn Asp Val Glu Ile
        275                 280                 285

Trp Lys Leu Phe Lys Asp Ile Thr Asn Gly Val Gln Gln Leu His Ser
    290                 295                 300

Ser His Ile Leu His Arg Asp Leu Lys Pro Ser Asn Cys Leu Leu Lys
305                 310                 315                 320

Tyr Arg Tyr Glu Lys Glu Val Thr Gln Leu Asp Glu Tyr Asn Asp Ile
                325                 330                 335

Pro Lys Val Met Val Ser Asp Phe Gly Glu Gly Thr Phe Asp Asn Ile
            340                 345                 350

Glu Arg Ser Ser Ser Gly Tyr Thr Gly Thr Leu Glu Phe Thr Ala Pro
        355                 360                 365

Glu Val Phe Gly Ser Asn Tyr Ser Arg Ala Ser Asp Val Tyr Ser Leu
    370                 375                 380

Gly Leu Ile Leu Tyr Phe Leu Cys Phe Gly Asp Leu Pro Tyr Lys Thr
385                 390                 395                 400

Gln Asp Ile Lys Arg Glu Ile Gln Gln Tyr Ala Lys Gly Glu Ser Asp
                405                 410                 415
```

```
Leu Phe Thr Glu Ile Asp Val Ile Arg Asn Asp Ile Ser Lys Asp Trp
            420                 425                 430

Val Lys Leu Ile Leu Glu Cys Cys Ser Leu Asp Ala Asp Lys Arg Pro
        435                 440                 445

Ser Ala Ser Glu Ile Leu Ala Asn Leu Asn Thr Ile Tyr Leu Gln Leu
    450                 455                 460

Glu Ala Lys Gln Gln Asn Lys Glu His Pro Glu Pro Glu Ala Tyr Gly
465                 470                 475                 480

Ile His Pro Pro Asp Ser Phe Asn Tyr Pro Lys Phe Leu Ala Val Ile
                485                 490                 495

Val Asn Val Leu Leu Lys Val Gln Gln Asn Thr Phe Lys Met Val
            500                 505                 510

Thr Cys Phe Ile Ile Gly Leu Ser Phe His Val Thr Thr Lys Asn Met
        515                 520                 525

Ile Met Leu Ser Val Leu Asn Ala Leu Phe Ser Val Leu Ser Ile Val
    530                 535                 540

Tyr Leu Asn Ser Asn
545

<210> SEQ ID NO 3
<211> LENGTH: 487
<212> TYPE: DNA
<213> ORGANISM: Komagataella pastoris
<220> FEATURE:
<223> OTHER INFORMATION: GAP promoter

<400> SEQUENCE: 3 tttttgtag aaatgtcttg gtgtcctcgt ccaatcaggt agccatctct gaaatatctg      60
gctccgttgc aactccgaac gacctgctgg caacgtaaaa ttctccgggg taaaacttaa     120
atgtggagta atggaaccag aaacgtctct tcccttctct ctccttccac cgcccgttac    180
cgtccctagg aaattttact ctgctggaga gcttcttcta cggccccctt gcagcaatgc    240
tcttcccagc attacgttgc gggtaaaacg gaggtcgtgt acccgaccta gcagcccagg    300
gatggaaaag tcccggccgt cgctggcaat aatagcgggc ggacgcatgt catgagatta    360
ttggaaacca ccagaatcga atataaaagg cgaacacctt tcccaatttt ggtttctcct    420
gacccaaaga ctttaaattt aatttatttg tccctatttc aatcaattga caactatca    480 aaacaca                                                                487

<210> SEQ ID NO 4
<211> LENGTH: 933
<212> TYPE: DNA
<213> ORGANISM: Komagataella pastoris
<220> FEATURE:
<223> OTHER INFORMATION: AOX1 promoter

<400> SEQUENCE: 4
aacatccaaa gacgaaaggt tgaatgaaac cttttgccat ccgacatcc acaggtccat       60 tctcacacat aagtgccaaa cgcaacagga ggggatacac tagcagcaga ccgttgcaaa    120
cgcaggacct ccactcctct tcctcaac acccacttttt gccatcgaaa accagccca    180 gttattgggc ttgattggag ctcgctcatt ccaattcctt ctattaggct actaacacca    240
tgactttatt agcctgtcta tcctggcccc cctggcgagg ttcatgtttg tttatttccg    300
aatgcaacaa gctccgcatt acaccgaac atcactccag atgagggctt tctgagtgtg    360 ggtcaaata gtttcatgtt ccccaaatgg cccaaaactg acagtttaaa cgctgtcttg    420
```

```
gaacctaata tgacaaaagc gtgatctcat ccaagatgaa ctaagtttgg ttcgttgaaa      480
tgctaacggc cagttggtca aaaagaaact tccaaaagtc ggcataccgt ttgtcttgtt      540
tggtattgat tgacgaatgc tcaaaaataa tctcattaat gcttagcgca gtctctctat      600
cgcttctgaa ccccggtgca cctgtgccga aacgcaaatg gggaaacacc cgcttttttgg     660 atgattatgc attgtctcca cattgtatgc ttccaagatt ctggtgggaa tactgctgat      720
agcctaacgt tcatgatcaa aatttaactg ttctaacccc tacttgacag caatatataa      780
acagaaggaa gctgccctgt cttaaacctt ttttttatca tcattattag cttactttca      840
taattgcgac tggttccaat tgacaagctt ttgattttaa cgactttttaa cgacaacttg    900 agaagatcaa aaacaacta attattcgaa acg                                    933
```

```
<210> SEQ ID NO 5
<211> LENGTH: 334
<212> TYPE: DNA
<213> ORGANISM: Komagataella pastoris
<220> FEATURE:
<223> OTHER INFORMATION: AOX1 terminator

<400> SEQUENCE: 5
ccttagacat gactgttcct cagttcaagt tgggcactta cgagaagacc ggtcttgcta       60
gattctaatc aagaggatgt cagaatgcca tttgcctgag agatgcaggc ttcattttttg     120 atacttttttt atttgtaacc tatatagtat aggatttttt ttgtcatttt gtttcttctc    180
gtacgagctt gctcctgatc agcctatctc gcagctgatg aatatcttgt ggtaggggtt    240
tgggaaaatc attcgagttt gatgttttttc ttggtatttc ccactcctct tcagagtaca   300
gaagattaag tgagacgttc gtttgtgcaa gctt                                 334
```

```
<210> SEQ ID NO 6
<211> LENGTH: 600
<212> TYPE: DNA
<213> ORGANISM: Komagataella pastoris
<220> FEATURE:
<223> OTHER INFORMATION: CCA38473 terminator

<400> SEQUENCE: 6
gacaataaga agaaaaaaaa agaaaagcgg tgggggaggg attattaaat aaggattatg       60 taacccccagg gtaccgttct atacatattt aaggattatt taggacaatc gatgaaatcg   120
gcatcaaact ggatgggagt atagtgtccg gataatcgga taaatcatct tgcgaggagc   180
cgcttggttg gttggtgaga ggagtgaaat atgtgtctcc tcacccaaga atcgcgatat    240
cagcaccctg tggggacac tattggcctc cctcccaaac cttcgatgtg gtagtgcttt     300
attatattga ttcattgat tacatagcta aaccctgcct ggttgcaagt tgagctccga    360
attccaatat tagtaaaatg cctgcaagat aacctcggta tggcgtccga ccccgcttaa    420
ttattttaac tcctttccaa cgaggacttc gtaatttttg attagggagt tgagaaacgg    480
ggggtcttga tacctcctcg atttcagatc ccaccccctc tcagtcccaa gtgggacccc    540
cctcggccgt gaaatgcgcg cactttagtt ttttttcgcat gtaaacgccg gtgtccgtca   600
```

```
<210> SEQ ID NO 7
<211> LENGTH: 1635
<212> TYPE: DNA
<213> ORGANISM: Komagataella pastoris
<220> FEATURE:
<223> OTHER INFORMATION: ARG4 gene
```

```
<400> SEQUENCE: 7
atggttgtgc gacagattca ctgtgaaaga ctgttcatta tacccacgtt tcactgggag      60
atgtaagcct taggtgtttt accctgatta gataatacaa taaccaacag aaatacgaga     120
atctaaacta atttcgatga ttcattttc tttttaccgc gctgcctctt ttggcaattc     180
tttcacctat attctacctt ctctttcctt ttgttctaaa cttattacca gctatctatg     240
tcgaatcaag aagaaggact taaactgtgg ggtggcaggt ttactgggc tactgaccccc     300 ttgatggatt tgtataacgc ttccttacct tacgacaaga aaatgtacaa ggtggattta     360
gaaggaacaa aagtttacac tgagggcctg gagaaaatta atttgctaac taaagacgaa     420
ctaagtgaga ttcatcgtgg tctcaaattg attgaagcag agtgggcaga agggaagttt     480
gttgagaagc caggggatga ggatattcac actgctaatg aacgtcgctt gggtgagttg     540
attggtcgtg gaatctctgg taaggttcat accggaaggt ctagaaatga tcaagttgcc     600
actgatatgc ggttgtatgt cagagacaat ctaactcagt tggctgacta tctgaagcag     660
ttcattcaag taatcatcaa gagagctgaa caggaaatag acgtcttgat gcccggttat     720
actcacttgc aaagagctca accaatcaga tggtctcact ggttgagcat gtatgctacc     780
tatttcactg aagattatga gagactgaat caaatcgtta aaaggttgaa caaatcccca     840
ttgggagctg gagctttggc tggtcatcct tatggaattg atcgtgaata cattgctgag     900
agattagggt tgattctgt tattggtaat tctttggccg ctgttcaga cagagatttt     960 gtagtcgaaa ccatgttctg gtcttcgttg tttatgaatc atatttctcg attctcagaa    1020
gatttgatca tttactccac tggagagttt ggatttatca agttggcaga tgcttattct    1080
actggatctt ctctgatgcc tcaaaaaaaa aacccagact ctttggagtt attgaggggt    1140
aaatctggta gatgttttgg ggccttggct ggtttcctca tgtctattaa gtccattccg    1200
tcaacctata acaaagatat gcaagaggat aaggagcctt tatttgatac tctaatcact    1260
gtagagcact cgattttgat agcatccggt gtagtttcta ccttgaacat tgatgccgaa    1320
cgaatgaaga atgctctaac tatggatatg ctggctacag atcttgccga ctatttagtt    1380
agaaggggag ttccattcag agaaactcac cacatttctg gtgaatgtgt cagacaagcc    1440
gaggagttga acctttctgg tattgatcag ttgtccctcg aacaattgaa atccattgac    1500
tcccgttttg aggctgatgt ggcttcaacg tttgactttg aagccagtgt tgaaaaaaga    1560
actgccaccg gaggaacttc taagactgct gtttttaaagc aattggatgc actgaatgaa    1620
aagctagagt cttga                                                     1635

<210> SEQ ID NO 8
<211> LENGTH: 2148
<212> TYPE: DNA
<213> ORGANISM: Komagataella pastoris

<400> SEQUENCE: 8
atgtcagtcg ttccgtacca aaaggaccta agggtggttt ggaagcatcc tgattccaga      60
tccgtagttc tctactccaa agagcatcag agcttccagt atatttcttt agacagagtt     120
gatgaagtca atggatcaga tagtgactat tttcacagta aaaacggaag taaccaacga     180
agaagatcat cgacagtatg tccgagatgt ggctttaata tgagtagatc atctccagaa     240
tccatgttca ataacaacta cttcaagctg cttgcaaacg ttcaaagcaa taaactatca     300
gagcaagaaa aagatagcca tatgaatttg ctcaatagcg ccataaagtt cccatccttt     360
aaattgaacc gatccacttt tccggacaat ctattcagtc agggctattt tgcaaagttc     420
```

```
ttcacagaat taaatgtttt ggggcatggt agtaacgggg tggtgctcaa agttgaacat    480
gtattgaatg attcatgtct cggggtattt gctctgaaga aaattagtat tggagagaag    540
ctctccaacc ttgaaaatgt tctcaacgag gtcaagatat tataccagtt aaccaacgca    600
gatgtgcaat taggaggcaa cctggttagt tataatcatg tctggctgga agttgatcaa    660
ccgactgatt tcggcccaaa ggtcccttgt gtgttcatct tatttgaata ctgtgatgga    720
ggagatttgg aaagcttcat tgatcggctt aaacacccca agctgacat agaacaggag    780
aaacaatata gaaggatggt aagaaaggga ctaactgcag aaagaggagt acacgagcct    840
cggtctctta acgacgtgga gatttggaaa ctgttcaaag atattacaaa tggtgttcaa    900
caattgcatt cttctcatat attacacaga gacttaaagc catctaattg tctattaaaa    960
tacaggtatg aaaaggaggt cacccagttg gatgagtata atgacattcc aaaagtcatg   1020
gtgagtgatt ttggagaggg aacttttgac aatatcgaac gttcctcgtc aggatacacc   1080
ggaaccttag agttcaccgc tccagaagtg tttggctcga actattcacg agctagtgat   1140
gtttattctc taggattgat cttatatttc ttgtgtttcg gtgaccttcc gtataaaaca   1200
caggatataa aaagagaaat tcaacaatac gctaaaggag aatcggacct ctttacagaa   1260
attgatgtta ttaggaacga tatctccaaa gattgggtca aactgattct tgaatgttgc   1320
tctttagacg cagataaacg gccttcagcc tcagaaatct tggcaaattt gaatactatt   1380
tacttgcaat tggaagccaa acaacaaaat aaagaacatc ctgagccaga agcatacggt   1440
atccacccct ctgattcgtt caactatcca aaatttcttg cagtgattgt aaatgtgtta   1500
ctactgaagg ttcaacaaaa cacattcaaa atggtaacat gtttcatcat tggcctatca   1560
tttcacgtta caaccaaaaa catgatcatg ctaagtgtgt tgaatgcgct tttttcggtg   1620
ctttcgattg tctatcttaa cagcaactag acttttttgct tttctgatcc aaatccaaag   1680
tctcccgaga ctcgacaaaa ataccgtcat ctatgctatc tacaatgtat ttgaataatt   1740
cgtcgactcc tgtaccttct tttgcacttg tcttaaaata tggtaccttc aacctttcaa   1800
ccgtttccga tatttgattg tcattctcat tcttggataa atctgactta ttgcccacta   1860
gtagaatctg tatcttatgt tcttctctgt tgtatgcctc taattcggct atccagaact   1920
ctgccttcgt caagctggat atatctgtga ggtcaaatac tattatggca acagaagcat   1980
ttctatagta cattggagcc agggattggt aacgctcttg accggcggtg tcccaaatct   2040
ggaaattaat tagcttcacc tcgtttgttt ctggatcagt tacatagtat ttcttgacaa   2100
taaaggcagc acctatagtg ctttctttat ctgcatcaaa agcgtttg               2148
```

<210> SEQ ID NO 9
<211> LENGTH: 39
<212> TYPE: DNA
<213> ORGANISM: Artificial
<220> FEATURE:
<223> OTHER INFORMATION: primer 1

<400> SEQUENCE: 9
ctgcaggtcg actctagatt ttttgtagaa atgtcttgg                              39

<210> SEQ ID NO 10
<211> LENGTH: 49
<212> TYPE: DNA
<213> ORGANISM: Artificial
<220> FEATURE:
<223> OTHER INFORMATION: primer 2

<400> SEQUENCE: 10
aaattgaagg aaatctcata ctagttgtgt tttgatagtt gttcaattg                49

<210> SEQ ID NO 11
<211> LENGTH: 31
<212> TYPE: DNA
<213> ORGANISM: Artificial
<220> FEATURE:
<223> OTHER INFORMATION: primer 3

<400> SEQUENCE: 11
ttaggatcca acatccaaag acgaaaggtt g                                   31

<210> SEQ ID NO 12
<211> LENGTH: 38
<212> TYPE: DNA
<213> ORGANISM: Artificial
<220> FEATURE:
<223> OTHER INFORMATION: primer 4

<400> SEQUENCE: 12
ttaactagtc gtttcgaata attagttgtt ttttgatc                            38

<210> SEQ ID NO 13
<211> LENGTH: 30
<212> TYPE: DNA
<213> ORGANISM: Artificial
<220> FEATURE:
<223> OTHER INFORMATION: primer 5

<400> SEQUENCE: 13
aaaaacgcgt ccttagacat gactgttcct                                     30

<210> SEQ ID NO 14
<211> LENGTH: 30
<212> TYPE: DNA
<213> ORGANISM: Artificial
<220> FEATURE:
<223> OTHER INFORMATION: primer 6

<400> SEQUENCE: 14
ggggagatct aagcttgcac aaacgaactt                                     30

<210> SEQ ID NO 15
<211> LENGTH: 50
<212> TYPE: DNA
<213> ORGANISM: Artificial
<220> FEATURE:
<223> OTHER INFORMATION: primer 7

<400> SEQUENCE: 15
cggccgcgga tccagatctt ctagagacaa taagaagaaa aaaaaagaaa               50

<210> SEQ ID NO 16
<211> LENGTH: 51
<212> TYPE: DNA
<213> ORGANISM: Artificial
<220> FEATURE:
<223> OTHER INFORMATION: primer 8

<400> SEQUENCE: 16
ttcttctgag cggggaattc tctagatgac ggacaccggc gtttacatgc g             51

```
<210> SEQ ID NO 17
<211> LENGTH: 48
<212> TYPE: DNA
<213> ORGANISM: Artificial
<220> FEATURE:
<223> OTHER INFORMATION: primer 9

<400> SEQUENCE: 17
gctatgacca tgattacgcc gctagccatg gttgtgcgac agattcac           48

<210> SEQ ID NO 18
<211> LENGTH: 47
<212> TYPE: DNA
<213> ORGANISM: Artificial
<220> FEATURE:
<223> OTHER INFORMATION: primer 10

<400> SEQUENCE: 18
gatcctctag agtcgacctg cagtcaagac tctagctttt cattcag            47

<210> SEQ ID NO 19
<211> LENGTH: 46
<212> TYPE: DNA
<213> ORGANISM: Artificial
<220> FEATURE:
<223> OTHER INFORMATION: primer 11

<400> SEQUENCE: 19
caactatcaa aacacaacta gtatgtcagt cgttccgtac caaaag             46

<210> SEQ ID NO 20
<211> LENGTH: 46
<212> TYPE: DNA
<213> ORGANISM: Artificial
<220> FEATURE:
<223> OTHER INFORMATION: primer 12

<400> SEQUENCE: 20
cgagctcggt acccggaagc ttcaaacgct tttgatgcag ataaag             46

<210> SEQ ID NO 21
<211> LENGTH: 255
<212> TYPE: DNA
<213> ORGANISM: Komagataella pastoris

<400> SEQUENCE: 21
atgagatttc cttcaatttt tactgcagtt ttattcgcag catcctccgc attagctgct    60
ccagtcaaca ctacaacaga agatgaaacg gcacaaattc cggctgaagc tgtcatcggt   120
tacttagatt tagaagggga tttcgatgtt gctgttttgc cattttccaa cagcacaaat   180
aacgggttat tgtttataaa tactactatt gccagcattg ctgctaaaga agaagggta    240 tctttggata aaaga                                                   255

<210> SEQ ID NO 22
<211> LENGTH: 35
<212> TYPE: DNA
<213> ORGANISM: Artificial
<220> FEATURE:
<223> OTHER INFORMATION: primer 13

<400> SEQUENCE: 22
ggggactagt atgagatttc cttcaatttt tactg                             35
```

<210> SEQ ID NO 23
<211> LENGTH: 47
<212> TYPE: DNA
<213> ORGANISM: Artificial
<220> FEATURE:
<223> OTHER INFORMATION: primer 14

<400> SEQUENCE: 23
aaaaagatct acgcgtctcg agtctttat ccaaagatac cccttct        47

<210> SEQ ID NO 24
<211> LENGTH: 855
<212> TYPE: DNA
<213> ORGANISM: Artificial
<220> FEATURE:
<223> OTHER INFORMATION: Zeocin resistance gene

<400> SEQUENCE: 24
cccacacacc atagcttcaa aatgtttcta ctcctttttt actcttccag attttctcgg        60
actccgcgca tcgccgtacc acttcaaaac acccaagcac agcatactaa attttccctc       120
tttcttcctc tagggtgtcg ttaattaccc gtactaaagg tttggaaaag aaaaaagaga       180
ccgcctcgtt tctttttctt cgtcgaaaaa ggcaataaaa attttatca cgtttcttt        240 tcttgaaatt tttttttta gttttttttct ctttcagtga cctccattga tatttaagtt       300
aataaacggt cttcaatttc tcaagtttca gtttcattt tcttgttcta ttacaacttt        360
ttttacttct tgttcattag aaagaaagca tagcaatcta atctaagggg cggtgttgac       420
aattaatcat cggcatagta tatcggcata gtataatacg acaaggtgag gaactaaacc       480
atggccaagt tgaccagtgc cgttccggtg ctcaccgcgc gcgacgtcgc cggagcggtc       540
gagttctgga ccgaccggct cgggttctcc cggacttcg tggaggacga cttcgccggt       600
gtggtccggg acgacgtgac cctgttcatc agcgcggtcc aggaccaggt ggtgccggac       660
aacaccctgg cctgggtgtg ggtgcgcggc ctggacgagc tgtacgccga gtggtcggag       720
gtcgtgtcca cgaacttccg ggacgcctcc gggccggcca tgaccgagat cggcgagcag       780 ccgtggggggc gggagttcgc cctgcgcgac ccggccggca actgcgtgca cttcgtggcc       840
gaggagcagg actga                                                        855

<210> SEQ ID NO 25
<211> LENGTH: 1081
<212> TYPE: DNA
<213> ORGANISM: Artificial
<220> FEATURE:
<223> OTHER INFORMATION: G418 resistance gene

<400> SEQUENCE: 25
tacagagctt tatatcacct tactgaacgc tagagtagac ccaattcccg gctcacacca        60
cccttacatg cagagctaac caataaggta attaattaac actatatagc tcgtggtgaa       120
cactggcccg gagtagtcat acgtgtaggt ttttggcgtg atgaaaatca ggtggcgcac       180
gacttttcgt aaagttcggg agggagtgct gcaaacggca tataaggacc agttttctc       240 gcacattatc aattgctctt tagtacaaag ataatataga aaccatatga ttgaacaaga       300
tggattgcac gcaggttctc cggccgcttg ggtggagagg ctattcggct atgactgggc       360
acaacagaca atcggctgct ctgatgccgc cgtgttccgg ctgtcagcgc aggggcgccc       420
ggttcttttt gtcaagaccg acctgtccgg tgccctgaat gaactgcagg acgaggcagc       480
gcggctatcg tggctggcca cgacgggcgt tccttgcgca gctgtgctcg acgttgtcac       540

| | |
|---|---:|
| tgaagcggga agggactggc tgctattggg cgaagtgccg gggcaggatc tcctgtcatc | 600 |
| tcaccttgct cctgccgaga aagtatccat catggctgat gcaatgcggc ggctgcatac | 660 |
| gcttgatccg gctacctgcc cattcgacca ccaagcgaaa catcgcatcg agcgagcacg | 720 |
| tactcggatg gaagccggtc ttgtcgatca ggatgatctg gacgaagagc atcaggggct | 780 |
| cgcgccagcc gaactgttcg ccaggctcaa ggcgcgcatg cccgacggcg aggatctcgt | 840 |
| cgtgacccat ggcgatgcct gcttgccgaa tatcatggtg aaaatggcc gcttttctgg | 900 |
| attcatcgac tgtggccggc tgggtgtggc ggaccgctat caggacatag cgttggctac | 960 |
| ccgtgatatt gctgaagagc ttggcggcga atgggctgac cgcttcctcg tgctttacgg | 1020 |
| tatcgccgct cccgattcgc agcgcatcgc cttctatcgc cttcttgacg agttcttctg | 1080 |
| a | 1081 |

<210> SEQ ID NO 26
<211> LENGTH: 726
<212> TYPE: DNA
<213> ORGANISM: Artificial
<220> FEATURE:
<223> OTHER INFORMATION: svFC gene

<400> SEQUENCE: 26

| | |
|---|---:|
| gacattcaat tgcaagaatc tggtccatcc ttggttaagc catcccagac tttgtccttg | 60 |
| acttgttccg ttactggtga ctccatcact tctgactact ggtcctggat cagaaagttc | 120 |
| ccaggtaaca gattggagta catgggttac gtttcttact ccggttccac ttactacaac | 180 |
| ccatccttga gtccagaat ctccatcaca agagacactt ccaagaacca gtactacttg | 240 |
| gacttgaact ccgttactac tgaggacact gctacttact actgtgctaa ctgggacggt | 300 |
| gattactggg gtcaaggtac tttggttact gtttctgctg gtggtggtgg atcaggtggt | 360 |
| ggtggttctg gtggtggtgg atcagacatc gttttgactc aatccccagc tactttgtcc | 420 |
| gttactccag gtaactctgt ttccttgtcc tgtagagctc cccagtccat cggtaacaac | 480 |
| ttgcactggt atcaacagaa gtctcacgag tccccaagat gttgatcaa gtacgcttct | 540 |
| caatccatct ccggtatccc atctagattc tctggttccg gttctggtac tgacttcact | 600 |
| ttgtccatca actccgttga gacagaggac ttcggtatgt acttctgtca acagtctaac | 660 |
| tcctggccat acactttcgg tggtggtact aagttggagt ataagcacca tcatccacc | 720 |
| cactag | 726 |

<210> SEQ ID NO 27
<211> LENGTH: 45
<212> TYPE: DNA
<213> ORGANISM: Artificial
<220> FEATURE:
<223> OTHER INFORMATION: HindIII NotI BamHI BglII XbaI EcoRI

<400> SEQUENCE: 27

| | |
|---|---:|
| ttttaagctt gcggccgcgg atccagatct tctagagaat tcaaa | 45 |

<210> SEQ ID NO 28
<211> LENGTH: 30
<212> TYPE: DNA
<213> ORGANISM: Artificial
<220> FEATURE:
<223> OTHER INFORMATION: primer 15

<400> SEQUENCE: 28

| | |
|---|---:|
| gggggaattc tacagagctt tatatcacct | 30 |

```
<210> SEQ ID NO 29
<211> LENGTH: 36
<212> TYPE: DNA
<213> ORGANISM: Artificial
<220> FEATURE:
<223> OTHER INFORMATION: primer 16

<400> SEQUENCE: 29
tttgaattcc ccgctcagaa gaactcgtca agaagg                                 36

<210> SEQ ID NO 30
<211> LENGTH: 26
<212> TYPE: DNA
<213> ORGANISM: Artificial
<220> FEATURE:
<223> OTHER INFORMATION: primer 17

<400> SEQUENCE: 30
gggtatcttt ggataaaaga ctcgag                                            26

<210> SEQ ID NO 31
<211> LENGTH: 48
<212> TYPE: DNA
<213> ORGANISM: Artificial
<220> FEATURE:
<223> OTHER INFORMATION: primer 18

<400> SEQUENCE: 31
aggaacagtc atgtctaagg acgcgtctag tggtggtgat gatggtgc                    48

<210> SEQ ID NO 32
<211> LENGTH: 6
<212> TYPE: PRT
<213> ORGANISM: Artificial
<220> FEATURE:
<223> OTHER INFORMATION: His tag

<400> SEQUENCE: 32

His His His His His His
1               5

<210> SEQ ID NO 33
<211> LENGTH: 45
<212> TYPE: DNA
<213> ORGANISM: Artificial
<220> FEATURE:
<223> OTHER INFORMATION: primer 19

<400> SEQUENCE: 33
ccgggtaccg agctcgaatt ccccacacac catagcttca aaatg                       45

<210> SEQ ID NO 34
<211> LENGTH: 44
<212> TYPE: DNA
<213> ORGANISM: Artificial
<220> FEATURE:
<223> OTHER INFORMATION: primer 20

<400> SEQUENCE: 34
gtaaaacgac ggccagtgaa ttctcagtcc tgctcctcgg ccac                        44

<210> SEQ ID NO 35
<211> LENGTH: 55
<212> TYPE: DNA
<213> ORGANISM: Artificial
<220> FEATURE:
<223> OTHER INFORMATION: primer 21
```

<400> SEQUENCE: 35
gctgaggttt aaacggccgg ccggcgcgcc agattagggt tgattctgt tattg    55

<210> SEQ ID NO 36
<211> LENGTH: 55
<212> TYPE: DNA
<213> ORGANISM: Artificial
<220> FEATURE:
<223> OTHER INFORMATION: primer 22

<400> SEQUENCE: 36
taatctggcg cgccggccgg ccgtttaaac ctcagcaatg tattcacgat caatt    55

<210> SEQ ID NO 37
<211> LENGTH: 23
<212> TYPE: DNA
<213> ORGANISM: Artificial
<220> FEATURE:
<223> OTHER INFORMATION: AscI-FseI-PmeI

<400> SEQUENCE: 37
ggcgcgccgg ccggccgttt aaa    23

<210> SEQ ID NO 38
<211> LENGTH: 981
<212> TYPE: DNA
<213> ORGANISM: Artificial
<220> FEATURE:
<223> OTHER INFORMATION: EGFP gene

<400> SEQUENCE: 38
atgagatttc cttcaatttt tactgcagtt ttattcgcag catcctccgc attagctgct    60
ccagtcaaca ctacaacaga agatgaaacg gcacaaattc cggctgaagc tgtcatcggt   120
tacttagatt tagaagggga tttcgatgtt gctgttttgc cattttccaa cagcacaaat   180
aacggggttat tgtttataaa tactactatt gccagcattg ctgctaaaga agaagggta   240
tctttggata aaagactcga gatggtttct aagggtgaag agttgttcac tggtgttgtt   300
ccaatcttgg ttgagttgga cggtgacgtt aacggacaca agttctctgt ttctggtgaa   360
ggtgagggtg acgctactta cggaaagttg actttgaagt tcatctgtac tactggtaag   420
ttgccagttc catggccaac tttggttact actttgactt acggtgttca gtgtttctcc   480
agatacccag accacatgaa gcagcacgat ttcttcaagt ctgctatgcc agagggttac   540
gttcaagaga gaactatctt cttcaaggac gacggtaact acaagactag agctgaggtt   600
aagttcgagg gtgacacatt ggttaacaga atcgagttga agggtatcga cttcaaagag   660
gacggaaaca tcttgggtca caagttggag tacaactaca actccacaa cgtttacatc   720
atggctgaca agcagaagaa cggtatcaag gttaacttca agatcagaca caacatcgag   780
gacggttccg ttcaattggc tgaccactac aacagaaca ctccaattgg tgacggtcca   840
gttttgttgc cagacaacca ctacttgtcc actcaatccg ctttgtccaa ggacccaaac   900
gagaagagag atcacatggt tttgttggag ttcgttactg ctgctggtat cactttgggt   960
atggacgagt tgtacaagta a    981

<210> SEQ ID NO 39
<211> LENGTH: 47
<212> TYPE: DNA
<213> ORGANISM: Artificial
<220> FEATURE:
<223> OTHER INFORMATION: primer 23

```
<400> SEQUENCE: 39
ctgcaggtcg actctagaac tagtatgaga tttccttcaa tttttac            47

<210> SEQ ID NO 40
<211> LENGTH: 40
<212> TYPE: DNA
<213> ORGANISM: Artificial
<220> FEATURE:
<223> OTHER INFORMATION: primer 24

<400> SEQUENCE: 40
cgagctcggt acccggctcg agttacttgt acaactcgtc                    40

<210> SEQ ID NO 41
<211> LENGTH: 42
<212> TYPE: DNA
<213> ORGANISM: Artificial
<220> FEATURE:
<223> OTHER INFORMATION: primer 25

<400> SEQUENCE: 41
cgagttgtac aagtaactcg agcttagaca tgactgttcc tc                 42

<210> SEQ ID NO 42
<211> LENGTH: 42
<212> TYPE: DNA
<213> ORGANISM: Artificial
<220> FEATURE:
<223> OTHER INFORMATION: primer 26

<400> SEQUENCE: 42
tcgagctcgg tacccggaag cttgcacaaa cgaacttctc ac                 42
```

CELL AND METHOD FOR PRODUCING TARGET PROTEIN USING SAME

TECHNICAL FIELD

One or more embodiments of the present invention relate to a novel cell that has improved the productivity of a target protein by activating a particular gene, a vector for activating a gene, and a method for producing a target protein using the novel cell.

BACKGROUND

Genetic recombination methods are widely used in the manufacture of industrially useful biomaterials such as antibodies, enzymes, and cytokines to be utilized in medical and diagnostic applications. Hosts for producing proteins of interest by genetic recombination methods include animals such as chicken, animal cells such as CHO, insects such as silkworm, insect cells such as sf9, and microorganisms such as yeast cells and *E. coli* cells. Yeast cells, among the hosts, are extremely beneficial and various studies have been conducted, since: large scale culture is possible in a low-cost medium at a high density, and thus the target protein may be produced at a low cost; a secretory expression into a culture medium is feasible with the use of a signal peptide, and thus the purification process of a target protein may be easy; and post-translational modifications such as glycosylation can be made due to being an eucaryote. If an innovative production technology which can be applied to various proteins of interest in yeast cells is developed, diverse industrial expansions can be hopefully expected.

*Komagataella pastoris*, a yeast species, is a methanol-utilizing yeast having an excellent protein expression ability and capable of utilizing a low-cost carbon source, which is advantageous in the industrial production. For example, Non-Patent Document 1 reports a method for producing exogenous proteins, such as phytase, trypsin, nitrate reductase, phospholipase C, collagen, proteinase K, Ecallantide (Kalbitor), Ocriplasmin (Jetrea), human insulin, single-chain antibodies, and human serum albumin, using *Komagataella pastoris*. For the production of exogenous proteins in yeast cells, various attempts have been made to improve the productivity, such as addition of a signal sequence, use of a strong promoter, codon modification, co-expression of chaperone genes, co-expression of transcription factor genes, inactivation of a protease gene derived from a host yeast, and studies on culture conditions. For example, Patent Document 1 reports the productivity improvement by expressing transcription factors that activate methanol-inducible promoters using *Komagataella pastoris*. Patent Document 2 also reports the productivity improvement by expressing a novel protein that increases the secretion amount of endogenous and exogenous proteins using *Komagataella pastoris*.

Meanwhile, in antibody pharmaceutical development, studies have been intensively performed for small molecular antibodies with relatively small molecular weights while retaining high specificity, such as diabodies that are composed of variable regions only, tandem scFv (taFv) in which two single-chain Fv (scFv) are linked, and single-domain antibodies (VFH). However, sufficient productivity has not been achieved (Non-Patent Document 2).

[Patent Document 1] WO 2012/102171
[Patent Document 2] WO 2017/170468
[Non-Patent Document 1] M. Ahmad et al., Appl Microbiol Biotechnol, 98, 5301-5317 (2014)
[Non-Patent Document 2] Y. Liu et al., Appl Microbiol Biotechnol, 102, 539-551 (2018)

SUMMARY

One or more embodiments of the present invention are to provide a novel means of improving productivity of a target protein.

The present inventors have identified a novel protein through an exhaustive analysis of the nucleotide sequence of chromosomal DNA of a yeast belonging to the genus *Komagataella*. Then, the present inventors have found that the productivity of a target protein in a cell is improved by activating a gene encoding the novel protein, and has completed one or more embodiments of the present invention.

That is, one or more embodiments of the present invention encompass the following aspects.

(1) A cell, wherein a gene comprising a nucleotide sequence of any one of (a) to (f) is activated:
(a) a nucleotide sequence set forth in SEQ ID NO: 1;
(b) a nucleotide sequence of a nucleic acid that hybridizes under a stringent condition to a nucleic acid consisting of a nucleotide sequence complementary to the nucleotide sequence set forth in SEQ ID NO: 1;
(c) a nucleotide sequence having 85% or higher sequence identity to the nucleotide sequence set forth in SEQ ID NO: 1;
(d) a nucleotide sequence encoding an amino acid sequence set forth in SEQ ID NO: 2;
(e) a nucleotide sequence encoding an amino acid sequence having 85% or higher sequence identity to the amino acid sequence set forth in SEQ ID NO: 2; and
(f) a nucleotide sequence encoding an amino acid sequence derived from the amino acid sequence set forth in SEQ ID NO: 2 by substitution, deletion, and/or addition of 1 or a plurality of amino acids.

(2) The cell according to (1), wherein the cell comprises a vector comprising:
a nucleotide sequence of any one of (a) to (f);
a nucleotide sequence having a homologous region to the nucleotide sequence of any one of (a) to (f);
a nucleotide sequence having a homologous region to a promoter for a gene comprising the nucleotide sequence of any one of (a) to (f); and/or
a nucleotide sequence having a homologous region to a terminator for a gene comprising the nucleotide sequence of any one of (a) to (f).

(3) The cell according to (1) or (2), wherein the cell comprises a vector comprising a nucleotide sequence encoding a target protein.

(4) The cell according to any one of (1) to (3), wherein the cell is a yeast cell, a bacterial cell, a fungal cell, an insect cell, an animal cell, or a plant cell.

(5) The cell according to (4), wherein the yeast cell is a methanol-utilizing yeast cell, a fission yeast cell, or a budding yeast cell.

(6) The cell according to (5), wherein the methanol-utilizing yeast cell is a cell of a yeast belonging to the genus *Komagataella* or a cell of a yeast belonging to the genus *Ogataea*.

(7) A method for producing a target protein, comprising a culture step of culturing the cell according to any one of (1) to (6), and a collecting step of collecting the target protein from a culture obtained in the culture step.

(8) The method according to (7), wherein the target protein is an antibody.

(9) A vector comprising a nucleotide sequence of any one of (a) to (f):
(a) a nucleotide sequence set forth in SEQ ID NO: 1;
(b) a nucleotide sequence of a nucleic acid that hybridizes under a stringent condition to a nucleic acid consisting of a nucleotide sequence complementary to the nucleotide sequence set forth in SEQ ID NO: 1;

(c) a nucleotide sequence having 85% or higher sequence identity to the nucleotide sequence set forth in SEQ ID NO: 1;
(d) a nucleotide sequence encoding an amino acid sequence set forth in SEQ ID NO: 2;
(e) a nucleotide sequence encoding an amino acid sequence having 85% or higher sequence identity to the amino acid sequence set forth in SEQ ID NO: 2; and
(f) a nucleotide sequence encoding an amino acid sequence derived from the amino acid sequence set forth in SEQ ID NO: 2 by substitution, deletion, and/or addition of 1 or a plurality of amino acids.
(10) The vector according to (9), further comprising a nucleotide sequence encoding a target protein such as an antibody.
(11) A kit comprising the vector according to (9) and a vector including a nucleotide sequence encoding a target protein such as an antibody.

The present description encompasses the contents disclosed in JP Patent Application No. 2018-058953, to which the present application claims the priority.

According to one or more embodiments of the present invention, an efficient method for producing a target protein is provided.

DETAILED DESCRIPTION OF THE EMBODIMENTS

Hereinafter, one or more embodiments of the present invention are described in detail.

In one aspect, one or more embodiments of the present invention relate to a cell in which a gene comprising a nucleotide sequence of any one of (a) to (f) is activated:
(a) a nucleotide sequence set forth in SEQ ID NO: 1;
(b) a nucleotide sequence of a nucleic acid that hybridizes under a stringent condition to a nucleic acid consisting of a nucleotide sequence complementary to the nucleotide sequence set forth in SEQ ID NO: 1;
(c) a nucleotide sequence having 85% or higher sequence identity to the nucleotide sequence set forth in SEQ ID NO: 1;
(d) a nucleotide sequence encoding an amino acid sequence set forth in SEQ ID NO: 2;
(e) a nucleotide sequence encoding an amino acid sequence having 85% or higher sequence identity to the amino acid sequence set forth in SEQ ID NO: 2; and
(f) a nucleotide sequence encoding an amino acid sequence derived from the amino acid sequence set forth in SEQ ID NO: 2 by substitution, deletion, and/or addition of 1 or a plurality of amino acids.

In (b), hybridization of two nucleic acids under stringent conditions means, for example, the following: nucleic acid Y can be referred to as the "nucleic acid that hybridizes under a stringent condition to nucleic acid X" when, for example, the nucleic acid Y can be obtained as a nucleic acid bound on a filter by using the filter to which the nucleic acid X is immobilized, and subjecting it to a hybridization with nucleic acid Y having 85% or higher sequence identity at 65° C. in the presence of 0.7 to 1.0 M NaCl, and then washing the filter under a condition of 65° C. using 2-fold concentration of an SSC solution (the composition of 1-fold concentration of the SSC solution is composed of 150 mM sodium chloride and 15 mM sodium citrate). Alternatively, the nucleic acid X and the nucleic acid Y can be said to "hybridize to each other under stringent conditions". As the concentration of the SSC solution decreases, the nucleic acid having higher sequence identity can be expected to hybridize. Thus, the nucleic acid Y is a nucleic acid that can be obtained as a nucleic acid bound on a filter by washing the filter with 1-fold concentration of the SSC solution at 65° C. with 0.5-fold concentration of the SSC solution at 65° C., with 0.2-fold concentration of the SSC solution at 65° C., or with 0.1-fold concentration of the SSC solution at 65° C. Also, as the temperature increase, the nucleic acid having higher sequence identity can be expected to hybridize. Thus, the nucleic acid Y is a nucleic acid that can be obtained as a nucleic acid bound on a filter by washing the filter with 2-fold concentration of the SSC solution at 70° C., with 2-fold concentration of the SSC solution at 75° C., with 2-fold concentration of the SSC solution at 80° C., or with 2-fold concentration of the SSC solution at 85° C. The standard nucleic acid X may be a colony or plaque-derived nucleic acid X. The number of nucleotide in the nucleotide sequence of (h) is, for example, 80% or higher, such as 85% or higher, 90% or higher, 9.5% or higher, 96% or higher, 97% or higher, 98% or higher, 99% or higher, or 100% of the number of nucleotide in the nucleotide sequence set forth in SEQ NO: 1.

In one or more embodiments of the present invention, nucleotide sequence and amino acid sequence identity can be determined using a method or sequence analysis software well known to a person skilled in the art. For example, the blastn program or blastp program of the BLAST algorithm or the fasta program of the FASTA algorithm can be used. In one or more embodiments of the present invention, the "sequence identity" between the target nucleotide sequence to be evaluated and the nucleotide sequence X is determined by aligning the nucleotide sequence X and the target nucleotide sequence to be evaluated, introducing a gap according to need, adjusting the degree of nucleotide consistency at the maximal level, and indicating a frequency of the identical nucleotides appearing at the identical sites in the nucleotide sequence including a gap portion in terms of percentage (%).

The sequence identity of the nucleotide sequence of (c) to the nucleotide sequence set forth in SEQ ID NO: 1 is 85% or higher, such as, 90% or higher, 95% or higher, 96% or higher, 97% or higher, 98% or higher, or 99% or higher.

The sequence identity of the amino acid sequence encoded by the nucleotide sequence of (e) to the amino acid sequence set forth in SEQ ID NO: 2 is 85% or higher, such as 90% or higher, 95% or higher, 96% or higher, 97% or higher, 98% or higher_ or 99% or higher.

In (f), "1 or a plurality of" refers to, for example, 1 to 80, such as 1 to 70, 1 to 60, 1 to 50, 1 to 40, 1 to 30, 1 to 20, 1 to 15, 1 to 10, 1 to 5, 1 to 4, 1 to 3, 1 to 2, or 1.

The "nucleic acid" in the present disclosure can also be referred to as "polynucleotide", and refers to DNA or RNA. The DNA may be single-stranded DNA or may be double-stranded DNA.

The "gene" in the present disclosure encompasses not only DNA, but also mRNA and cDNA, of the nucleic acids that a host cell possesses, but can typically be DNA, particularly genomic DNA. The "gene" can be a gene of any functional region, and, for example, the gene may include an exon only, or may include an exon and an intron. In one or more embodiments in which the "gene" is RNA, any one or more or all thymine (T) in the nucleotide sequence of (a) to (f) can be replaced with uracil (U).

When the nucleotide sequences of (a) to (f) each are a nucleotide sequence in Which a plurality of exons are joined to form the sequence (e.g., a cDNA nucleotide sequence), the genes comprising the nucleotide sequence of (a) to (f) each may be a DNA or RNA comprising a nucleotide sequence in which one or more intron nucleotide sequences are further inserted and/or added to the nucleotide sequence.

In one or more embodiments, the nucleotide sequences of (b), (c), (e), and (f) encode polypeptides having equivalent activity to a polypeptide consisting of the amino acid sequence set forth in SEQ ID NO: 2. The equivalent activity refers to an activity that is 70% or higher, such as 80% or higher, 90% or higher, 100% or higher, and 200% or less, 150% or less, 120% or less, compared to the activity of the polypeptide consisting of the amino acid sequence set forth in SEQ ID NO: 2. Herein, the activity of a polypeptide consisting of an amino acid sequence set forth in SEQ ID NO: 2 refers to activity that improves the productivity of a target protein in a cell. The polypeptides encoded by the nucleotide sequences of (b), (c), (e), and (f) have the activity that improves the productivity of a target protein in a cell, as does the polypeptide consisting of an amino acid sequence set forth in SEQ ID NO: 2. Specifically, the production amount of the target protein by the cell in which the gene comprising the nucleotide sequence of (b), (c), (e), or (f) is activated can be equivalent to the production amount of the target protein by the cell in which the gene comprising the nucleotide sequence of (a) or (d) is activated. For example, the activity of the former can be 70% or higher, such as 80% or higher, 90% or higher, 100% or higher, and 200% or less, 150% or less, 120% or less compared to the latter.

In the present disclosure, the "nucleotide sequence encoding an amino acid sequence" refers to a nucleotide sequence designed based on a codon table for a polypeptide consisting of an amino acid sequence, wherein the nucleotide sequence produces a polypeptide by transcription and translation.

The "polypeptide" refers to those in which two or more amino acids are peptide bonded, and includes, in addition to proteins, those having a short chain length called as peptides or oligopeptides.

The "activated" refers to a state in which the function of the gene is obtained or is enhanced, a state in which the function of the gene is enhanced. The "activated" also encompasses a state in which the expression level of the gene transcription product mRNA or the gene translation product polypeptide is elevated, and a state in which the gene is functioning normally as an mRNA or protein, and is a state in which the expression level of the gene transcription product mRNA or the gene translation product polypeptide is elevated. Here, the "state in which the function of the gene is enhanced" and the "state in which the expression level of the gene transcription product mRNA or the gene translation product polypeptide is elevated" refers to a state in which the cell of the present disclosure is in the "state in which the function of the gene is enhanced" or the "state in which the expression level of the gene transcription product mRNA or the gene translation product polypeptide is elevated" as compared to a cell (parent strain) which has not been treated to activate a gene comprising the nucleotide sequence of any one of (a) to (f). Note that the expression level of mRNA can be quantified using a real-time PCR method, an RNA-Seq method, a Northern hybridization method, a hybridization method using a DNA array, or other methods, and the expression level of the polypeptide can be quantified using an antibody that recognizes the polypeptide, a staining compound having binding properties to the polypeptide, or other method. In addition to the quantitative methods described above, other conventional methods used by those skilled in the art can also be used.

As means for activating the gene, transformation by a vector comprising a nucleotide sequence corresponding to the gene, DNA mutation treatment using an agent or ultraviolet light, site-specific mutagenesis using PCR, RNAi, protease, and homologous recombination can be used. Activation of the gene may be performed by modification (deletion, substitution, addition, or insertion) of a nucleotide sequence in an ORF of the gene, modification (deletion, substitution, addition, or insertion) of a nucleotide sequence in a region that controls transcription initiation or arrest, such as a promoter region, an enhancer region, or a terminator region, transformation by a vector comprising a nucleotide sequence corresponding to the gene, and/or transformation by a vector comprising a nucleotide sequence having a homologous region to the gene. It should be noted that the site at which the deletion, substitution, addition, or insertion is performed, and the nucleotide sequence to be deleted, substituted, added, or inserted are not particularly limited as long as the normal function of the gene is obtained. The gene to be activated may be a chromosomal gene of the cell or may be an extrachromosomal gene of the cell.

The "modification of a nucleotide sequence" in the present disclosure can be performed using a technique such as gene insertion utilizing homologous recombination or site-specific mutagenesis. Examples of the modification include substitution of a promoter for a gene with a more active promoter, substitution of a terminator for a gene with a more active terminator, and alteration of a codon into a codon suitable for a cell. The "promoter" herein refers to a nucleotide sequence, for example, located upstream of a gene that is desired to be activated in the chromosomal genomic DNA of a cell, and is a nucleotide sequence that modulates the expression level of the gene product, and refers to a nucleotide sequence up to 5000 bp upstream from the start codon of a gene comprising the nucleotide sequence of any one of (a) to (f). The "terminator" refers to a nucleotide sequence, for example, located downstream of a gene that is desired to be activated in the chromosomal genomic DNA of a cell, and is a nucleotide sequence that modulates the expression level of the gene product. The "terminator" specifically refers to a nucleotide sequence up to 5000 bp downstream from the stop codon of a gene comprising the nucleotide sequence of any one of (a) to (f), and examples thereof include a nucleotide sequence of any one of (a1) to (c1) described below, wherein the nucleotide sequence has a function as a terminator.

The degree of increase in expression level of a gene comprising the nucleotide sequence of any one of (a) to (f) by activation in one or more embodiments of the present invention is not particularly limited as long as the productivity of the target protein is improved, but the expression level may be increased 5% or higher, 10% or higher, 20% or higher, 30% or higher, 40% or higher, 50% or higher, 60% or higher, 70% or higher, 80% or higher, 90% or higher, or 95% or higher compared to a cell that has not been treated to activate a gene comprising the nucleotide sequence of any one of (a) to (f). It should be noted that it is well known to those skilled in the art that, even when the expression level is not increased, the activation can be achieved as long as the normal function of the gene product is obtained, as described above, thus the degree of increase in expression level is only one of the criteria for determining activation.

The "gene comprising the nucleotide sequence set forth in SEQ ID NO: 1" has been found through an exhaustive analysis of the nucleotide sequences of four chromosomal DNAs of *Komagataella pastoris* (strain ATCC76273: ACCESSION No. FR83962.8 to FR839631 (J. Biotechnol. 154(4), 312-320 (2011), and strain GS115: ACCESSION No. FN392319 to FN392322 (Nat. Biotechnol. 27(6), 561-

566 (2009))). Specifically, the present inventors explored a polypeptide that improves the productivity of a target protein by activation, and a polynucleotide comprising a nucleotide sequence encoding an amino acid sequence of the polypeptide. As a result, the present inventors have found, in the strain ATCC76273, a polypeptide shown by an amino acid sequence set forth in SEQ ID NO: 2 (ACCESSION No. CCA37552) and a polynucleotide comprising a nucleotide sequence set forth in SEQ ID NO: 1 encoding the polypeptide. In the Examples described below, the present inventors introduced a vector that activates a gene consisting of the nucleotide sequence described above into a host cell, and confirmed that the productivity of a target protein is improved.

Herein, the increase in production amount of a target protein from a cell may be, for example, 1.01 times or more, 1.02 times or more, 1.03 times or more, 1.04 times or more, 1.05 times or more, 1.1 times or more, 1.2 times or more, 1.3 times or more, 1.4 times or more, 1.5 times or more, 1.6 times or more, 1.7 times or more, 1.8 times or more, 1.9 times or more, 2 times or more, 2.5 times or more, 3 times or more, 3.5 times or more, 4 times or more, 4.5 times or more, or 5 times or more, and 100 times or less, 90 times or less, 80 times or less, 70 times or less, 60 times or less, 50 times or less, 40 times or less. 30 times or less, 20 times or less, 10 times or less, 9 times or less, 8 times or less, 7 times or less, 6 times or less, or 5 times or less, relative to the production amount of a target protein in a cell that has not been treated to activate a gene comprising the nucleotide sequence of any one of (a) to (f) described above. When a target protein is produced by secretion, the secretion production amount can be easily determined by analyzing the cell culture supernatants using a method known to those skilled in the art, such as the Bradford method, the Lowry method, the BCA method, and the ELISA method.

In one or more embodiments of the present invention, a cell comprising a predetermined vector refers to a cell obtained by transformation with the predetermined vector or a progeny cell thereof.

The cell according to one or more embodiments of the present invention, in which a gene comprising a nucleotide sequence of any one of (a) to (f) is activated, is typically a cell comprising a vector comprising:

(I) a nucleotide sequence of any one of (a) to (f);

(II) a nucleotide sequence having a homologous region to the nucleotide sequence of any one of (a) to (f);

(III) a nucleotide sequence having a homologous region to a promoter for a gene comprising the nucleotide sequence of any one of (a) to (f); and/or (IV) a nucleotide sequence having a homologous region to a terminator for a gene comprising the nucleotide sequence of any one of (a) to (f), a cell comprising a vector comprising (I).

Transforming a cell with a vector comprising one or more nucleotide sequences of (I) to (IV) can activate a gene comprising the nucleotide sequence of any one of (a) to (f). The vectors comprising a plurality of the nucleotide sequences may be used as a vector in which a plurality of the nucleotide sequences are incorporated into one vector, or may be used as a plurality of vectors each containing one of the nucleotide sequences.

The "nucleotide sequence having a homologous region" of the present disclosure may be any nucleotide sequence having at least a portion of the nucleotide sequence of interest and having 50% or higher sequence identity. The sequence identity is 70% or higher, such as 80% or higher, 85% or higher, 90% or higher, 95% or higher, or 100%. The length of the nucleotide sequence having the homologous region is not particularly limited as long as the nucleotide sequence having a homologous region to a nucleotide sequence of interest is 20 bp or more because such nucleotide sequence can be homologously recombined. Specifically, the length is 0.1% or more, such as 0.5% or more, 1% or more, 1.5% or more, 2% or more, 2.5% or more, 3% or more, 3.5% or more, 4% or more, 4.5% or more, 5% or more, 5.5% or more, 6% or more, 6.5% or more, 7% or more, 7.5% or more, 8% or more, 8.5% or more, 9% or more, 9.5% or more, 10% or more, 15% or more, 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 95% or more, or 100% of the length of the nucleotide sequence of interest.

The vector comprising one or more nucleotide sequences of (I) to (IV) can be used as a vector that increases the number of copies in a host cell of a gene comprising the nucleotide sequence of any one of (a) to (f) or an expression cassette comprising the gene, relative to that in the parent strain.

In the Examples descried below, a nucleotide sequence (SEQ ID NO: 8) in which a terminator is linked to a gene consisting of the nucleotide sequence set forth in SEQ ID NO: 1 was prepared as a product by PCR with primers 11 and 12 using a chromosomal DNA mixture of *Komagataella pastoris* strain ATCC76273 as a template, the product was inserted downstream of a GAP promoter of a vector, and the newly constructed vector was used to transform a yeast belonging to the genus *Komagataella*, thereby activating the gene comprising the nucleotide sequence set forth in SEQ ID NO: 1 has been successfully achieved.

The vector according to one or more embodiments of the present invention can be in the form of, for example, a cyclic vector, a linear vector, or an artificial chromosome.

In the present disclosure, the "vector" is an artificially constructed nucleic acid molecule. The nucleic acid molecule constituting the vector of one or more embodiments of the present invention is usually DNA, double-stranded DNA, and may be cyclic or linear. In addition to any one or more nucleotide sequences of (I) to (IV), the "vector" used in one or more embodiments of the present invention can typically comprise a cloning site comprising one or more restriction enzyme recognition sites, an overlap region for use of an In-Fusion Cloning System (Clontech) or a Gibson Assembly System (New England Biolabs), a nucleotide sequence of an endogenous gene, a nucleotide sequence encoding a polypeptide consisting of an amino acid sequence of a target protein, a nucleotide sequence of a selection marker gene (such as a auxotrophic complementarity gene, or a drug resistance gene), or other nucleotide sequences. The scope of the vectors of one or more embodiments of the present invention encompasses not only nucleic acid molecules in the form in which the above-described nucleotide sequences, such as cloning site, overlap region, nucleotide sequence of foreign or endogenous gene, nucleotide sequence of a selected marker gene, have already been added, but also nucleic acid molecules in the form to which these nucleotide sequences can be added (e.g., a form comprising a cloning site including one or more restriction enzyme recognition sites to which these sequences can be added). The vector of one or more embodiments of the present invention is typically composed of a nucleic acid fragment comprising any one or more nucleotide sequences of (I) to (IV) linked to one or more other functional nucleic acid fragments as described above at both ends or at one end thereof, for example, via a restriction enzyme recognition site.

Examples of the linear vectors include a PCR product having a nucleotide sequence of an auxotrophic complementarity gene such as a URA3 gene, a LEU2 gene, a ADE1 gene, a HIS4 gene, or a ARG4 gene, or of a drug resistance gene such as a G418 resistance gene, a Zeocin™ resistance gene, a hygromycin resistance gene, a Clone NAT resistance gene, or a blasticidin S-resistance gene, or a vector linearized by cleaving a cyclic vector or a plasmid with an appropriate restriction enzyme.

A nucleotide sequence encoding a polypeptide in any one or more nucleotide sequences of (I) to (IV) or a nucleotide sequence encoding a target protein described below (hereinafter, collectively referred to as a "polypeptide-encoding nucleotide sequence") is included in the vector in a form inserted into an expression cassette. The "expression cassette" refers to an expression system that comprises the polypeptide-encoding nucleotide sequence and is capable of providing the state to express it as a polypeptide. The "state to express" refers to a state in which the polypeptide-encoding nucleotide sequence comprised in the expression cassette is arranged under the control of the elements required for gene expression in such a way as to be expressed in a transformant. Examples of the element required for gene expression include a promoter and a terminator.

The "promoter" herein refers to a nucleotide sequence region located upstream of the polypeptide-encoding nucleotide sequence, wherein various transcription regulators involved in promoting or suppressing transcription, in addition to an RNA polymerase, binds to or work with the region to read the polypeptide-encoding nucleotide sequence which is a template, whereby a complementary RNA is synthesized (transcribed).

For the promoter expressing a polypeptide, a promoter achieving the expression under the presence of a selected carbon source may be suitably used, and is not particularly limited.

When the carbon source is methanol, examples of the promoter for expressing the polypeptide include, but are not limited to, an AOX1 promoter, an AOX2 promoter, a CAT promoter, a DHAS promoter, an FDH promoter, an FMD promoter, a GAP promoter, and an MOX promoter.

When the carbon source is glucose or glycerol, examples of the promoter for expressing the polypeptide include, but are not limited to, a GAP promoter, a TEF promoter, a LEU2 promoter, a URA3 promoter, an ADE promoter, an ADH1 promoter, and a PGK1 promoter.

The vector comprising the nucleotide sequence of any one of (a) to (f) can further comprise a nucleotide sequence having a function as a terminator linked to a downstream side of the nucleotide sequence of any one of (a) to (f).

Examples of the nucleotide sequence having a function as a terminator include a nucleotide sequence of any one of the following (a1) to (c1):

(a1) a nucleotide sequence of positions 1651-2148 of SEQ ID NO: 8 or a partial nucleotide sequence thereof;
(b1) a nucleotide sequence of a nucleic acid that hybridizes under stringent conditions to a nucleic acid consisting of a nucleotide sequence complementary to the nucleotide sequence of positions 1651-2148 of SEQ ID NO: 8 or a partial nucleotide sequence thereof;
(c1) a nucleotide sequence having 85% or higher sequence identity to the nucleotide sequence of positions 1651-2148 of SEQ ID NO: 8 or a partial nucleotide sequence thereof.

The partial nucleotide sequence in (a1) is, for example, a partial contiguous nucleotide sequence in the nucleotide sequence of positions 1651-2148 of SEQ ID NO: 8 wherein the number of nucleotides of the partial contiguous nucleotide sequence is 70% or more, 80% or more, 90% or more, 95% or more, 96% or more, 97% or more, 98% or more, or 99% or more of the number of nucleotides of the nucleotide sequence of positions 1651-2148 of SEQ ID NO: 8.

In (b1), hybridization of two nucleic acids under stringent conditions is as described with respect to the nucleotide sequence of (h) of one or more embodiments of the present invention. The number of nucleotides of the nucleotide sequence of (b1) is, for example, 80% or more, 85% or more, 90% or more, 95% or more, 96% or more, 97% or more, 98% or more, 99% or more, or 100% of the nucleotide sequence of positions 1651-2148 of SEQ ID NO: 8 or a partial nucleotide sequence thereof.

The sequence identity in (c1) can be 85% or higher, for example 90% or higher, 95% or higher, or 96% or higher, specifically 97% or higher, 98% or higher, or 99% or higher.

In (a1), (b1), and (c1), the "nucleotide sequence of positions 1651-2148 of SEQ ID NO: 8 or a partial nucleotide sequence thereof" can be, for example, the "nucleotide sequence of positions 1651-2148 of SEQ ID NO: 8".

The method for producing the vector of one or more embodiments of the present invention is not particularly limited, but for example, a total synthesis method, a PCR method, the In-Fusion Cloning System (Clontech) or the Gibson Assembly System (New England Biolabs) can be used.

The "transformation" refers to introducing a vector into a cell. As the method for introducing the vector into a cell, i.e., the transformation method, known methods can be employed as appropriate. When a yeast cell is used as a host, examples thereof include, but are not limited to, an electroporation method, a lithium acetate method, and a spheroplast method.

In the present disclosure, the "cell" refers to a basic unit constituting an organism, and is not particularly limited as long as the gene is activated. Examples of the cell may include a yeast cell, a bacterial cell, a fungal cell, an insect cell, an animal cell, and a plant cell, and the yeast cell. The yeast cell may include a methanol-utilizing yeast cell, a fission yeast cell, or a budding yeast. The methanol-utilizing yeast cell may include a cell of a yeast belonging to the genus *Komagataella* or a cell of a yeast belonging to the genus *Ogataea*.

The methanol-utilizing yeast cell according to one or more embodiments of the present invention is defined as a yeast cell which can be cultured by utilizing methanol as the only carbon source, but a yeast which originally was a methanol-utilizing yeast cell but lost the methanol-utilizing ability due to an artificial modification or mutation is also encompassed by the methanol-utilizing yeast cell according to one or more embodiments of the present invention.

Examples of the methanol-utilizing yeast cell include cells of yeasts belonging to the genus *Pichia*, the genus *Ogataea*, and the genus *Komagataella*. Examples of the genus *Pichia* include *Pichia methanolica*. Examples of the genus *Ogataea* include *Ogataea angusta, Ogataea polymorpha, Ogataea parapolymorpha*, and *Ogataea minuta*. Examples of the genus *Komagataella* include *Komagataella pastoris*, and *Komagataella phaffii*.

The yeast cell belonging to the genus *Komagataella* may include cells belonging to *Komagataella pastoris* and *Komagataella phaffii*. *Komagataella pastoris* and *Komagataella phaffii* both have another name as *Pichia pastoris*.

Specific examples of the strains to be used as the host cells include *Komagataella pastoris* strain ATCC 76273 (Y-11430, CBS 7435) and *Komagataella pastoris* X-33 strain. These strains are available, for example, from the American Type Culture Collection, Thermo Fisher Scientific Inc.

Furthermore, in one or more embodiments of the present invention, strains derived from these strains of yeasts belonging to the genus *Komagataella* can also be used. An example of a histidine auxotrophic strain is the *Komagataella pastoris* GS115 strain (available from Thermo Fisher Scientific). In one or more embodiments of the present invention, strains derived from these strains can also be used.

One or more embodiments of the present invention relate to a method for producing a target protein, comprising a culture step of culturing the cell, and a collecting step of collecting the target protein from a culture obtained in the culture step.

Here, the "culture obtained in the culture step" is any culture that may comprise a target protein, such as a culture supernatant, a culture cell, a culture cell debris, or other types of culture products. Thus, examples of the method for producing a target protein include a method of culturing a cell described above and allowing the target protein to accumulate in the cell and a method comprising allowing the target protein to be secreted and accumulate in the culture supernatant.

The culture conditions of the cell are not particularly limited and may be appropriately selected depending on the cell. In the culture, any culture medium containing a nutrient source that can be utilized by the cell can be used. The culture can be performed by either batch culture or continuous culture.

In the present disclosure, the "target protein" is a protein produced by a cell in which the gene is activated, and the target protein may be an endogenous protein of the cell, or may be an exogenous protein. Examples of the target protein include enzymes derived from microorganisms, and proteins produced by animals and plants that are multicellular organisms. Examples thereof include, but are not limited to, phytase, protein A, protein G, protein L, amylase, glucosidase, cellulase, lipase, protease, glutaminase, peptidase, nuclease, oxidase, lactase, xylanase, trypsin, pectinase, isomerase, fibroin, and fluorescent protein. Proteins for treating human and/or animals are particularly used. Specific examples of the proteins for treating human and/or animals include hepatitis B virus surface antigen, hirudin, an antibody, a human antibody, a partial antibody, a human partial antibody, serum albumin, human serum albumin, epithelial growth factor, human epithelial growth factor, insulin, a growth hormone, erythropoietin, interferon, blood coagulation factor VIII, granulocyte colony stimulating factor (G-CSF), granulocyte macrophage colony stimulating factor (GM-CSF), thrombopoietin, IL-1, IL-6, tissue plasminogen activating factor (TPA), urokinase, leptin, and stem cell growth factor (SCF). Antibodies are particularly used.

In one or more embodiments of the present invention, each "antibody" may belong to any class, such as immunoglobulin G (IgG), immunoglobulin M (IgM), immunoglobulin D (IgD), immunoglobulin E (IgE), or immunoglobulin A (IgA), but is typically immunoglobulin G.

Immunoglobulin is a heterotetramer protein comprising two heavy chains and two light chains in a full-length state. The heavy and light chains each are composed of a variable region involved in antigen binding and a constant region.

The cell of one or more embodiments of the present invention may be a cell comprising a vector comprising a nucleotide sequence encoding a target protein, as desired. A "vector comprising a nucleotide sequence encoding a target protein" may be a vector further comprising a nucleotide sequence encoding a target protein in addition to the one or more nucleotide sequences of (I) to (IV), or may be a vector comprising a nucleotide sequence encoding a target protein, independently from a vector comprising the any one or more nucleotide sequences of (I) to (IV). One or more embodiments of a vector comprising a nucleotide sequence encoding a target protein and a transformation method using the same are similar to those described for the vector comprising any one or more nucleotide sequences of (I) to (IV).

When a non-secretable target protein is secreted extracellularly, a nucleotide sequence encoding a signal sequence at the 5' end of the nucleotide sequence encoding the target protein in a vector may be introduced. The nucleotide sequence encoding a signal sequence is not particularly limited as long as the nucleotide sequence encodes a signal sequence which can be expressed and secreted by a yeast. Examples thereof include nucleotide sequences encoding the signal sequences of Mating Factor alpha (MFα) of *Saccharomyces cerevisiae*, acidic phosphatase (PHO1) of *Ogataea angusta*, acidic phosphatase (PHO1) of *Komagataella pastoris*, invertase (SUC2) of *Saccharomyces cerevisiae*, PLB1 of *Saccharomyces cerevisiae*, bovine serum albumin (BSA), human serum albumin (HSA), and immunoglobulin.

EXAMPLES

Hereinafter, one or more embodiments of the present invention are described in detail by way of Production Examples and Examples, but one or more embodiments of the present invention are not limited by these.

The characteristics of the amino acid sequences and the nucleotide sequences shown in the sequence listing are summarized in the following table. In the remarks of the table, Fw means a forward primer and Re means a reverse primer.

TABLE 1

| SEQ ID NO: | Name | Remarks |
|---|---|---|
| 1 | Gene encoding novel protein (CCA37552) | |
| 2 | Novel protein (CCA37552) | |
| 3 | GAP promoter | |
| 4 | AOX1 promoter | |
| 5 | AOX1 terminator | |
| 6 | CCA38473 terminator | |
| 7 | ARG4 gene under promoter control | Parg4_CCA36851 |

TABLE 1-continued

| SEQ ID NO: | Name | Remarks |
|---|---|---|
| 8 | Gene encoding novel protein linked to terminator | |
| 9 | Primer 1 | PstI PgapFw |
| 10 | Primer 2 | SpeI Pgap Re |
| 11 | Primer 3 | BamHI Paox1 Fw |
| 12 | Primer 4 | SpeI Paox1 Re |
| 13 | Primer 5 | MluI Taox1 Fw |
| 14 | Primer 6 | BglII Taox1 Re |
| 15 | Primer 7 | NotI (partial) BamHI BglII XbaI CCA38473 terminator Fw |
| 16 | Primer 8 | G418 (partial) EcoRI XbaI CCA38473 terminator Re |
| 17 | Primer 9 | NheI Parg4 Fw |
| 18 | Primer 10 | PstI ARG4 Re |
| 19 | Primer 11 | SpeI CCA37552 Fw |
| 20 | Primer 12 | HindIII T37552 Re |
| 21 | Secretory signal MFα gene | |
| 22 | Primer 13 | SpaI MFα gene sequence Fw |
| 23 | Primer 14 | BglII MluI XhoI MFα gene sequence Re |
| 24 | Zeocin(TM) resistance gene under promoter control | Ptef_Zeo |
| 25 | G418 resistance gene under promoter control | HpPgap_G418 |
| 26 | Anti-lysozyme single-chain antibody gene | |
| 27 | Gene fragment having multicloning site of HindIII-NotI-BamHI-BglII-XbaI-EcoRI | HindIII NotI BamHI BglII XbaI EcoRI |
| 28 | Primer 15 | EcoRI HpPgap Fw |
| 29 | Primer 16 | EcoRI G418 Re |
| 30 | Primer 17 | MFα XhoI scFv Fw |
| 31 | Primer 18 | Taox1 MluI His6 Re |
| 32 | His tag | |
| 33 | Primer 19 | EcoRI Ptef Fw |
| 34 | Primer 26 | EcoRI Zeo Re |
| 35 | Primer 21 | AscI FseI PmeI Arg4 first half Re |
| 39 | Primer 22 | AscI FseI PmeI Arg4 second half Fw |
| 37 | AscI-FseI-PmeI | |
| 38 | EGFP gene | |
| 39 | Rimer 23 | SpeI EGFP Fw |
| 40 | Primer 24 | XhoI EGFP Re |
| 41 | Primer 25 | XhoI Taox1 Fw |
| 42 | Primer 26 | HindIII Taox1 Re |

Production Example 1

Preparation of Various Genes Used for Preparing Vectors

Detailed manipulation methods and the like for recombinant DNA techniques used in Examples below are described in the following literature: Molecular Cloning 2nd Edition (Cold Spring Harbor Laboratory Press, 1989), Current Protocols in Molecular Biology (Greene Publishing Associates and Wiley-Interscience).

In the following Examples, plasmids used to transform yeasts were prepared by introducing the constructed vector into *E. coli* DH5α, competency cells (manufactured by Takara Bio Inc.) and culturing and amplifying the obtained transformants. Preparation of plasmid from strain carrying the plasmid was performed using a FastGene Plasmid Mini Kit (manufactured by Nippon Genetics Co., Ltd).

A GAP promoter (SEQ ID NO: 3), an AOX1 promoter (SEQ ID NO: 4), an AOX1 terminator (SEQ ID NO: 5), a CCA38473 terminator (SEQ ID NO: 6), an ARG4 gene under promoter control (SEQ ID NO: 7), a gene encoding a novel protein (amino acid sequence set forth in SEQ ID NO: 2 (ACCESSION No. CCA37552)) linked to a terminator (SEQ ID NO: 8) were used for vector construction. These sequences were prepared by PCR using a mixture of chromosomal DNA of *Komagataella pastoris* strain ATCC76273 (the nucleotide sequence thereof is described in the European Molecular Biology Laboratory (EMBL) ACCESSION No. FR839628 to FR839631) as a template. The GAP promoter was prepared by PCR with primer 1 (SEQ ID NO: 9) and primer 2 (SEQ ID NO: 10). The AOX1 promoter was prepared by PCR with primer 3 (SEQ ID NO: 11) and primer 4 (SEQ ID NO: 12). The AOX1 terminator was prepared by PCR with primer 5 (SEQ ID NO: 13) and primer 6 (SEQ ID NO: 14). The CCA38473 terminator was prepared by PCR with primer 7 (SEQ ID NO: 15) and primer 8 (SEQ ID NO: 16). The ARG4 gene under promoter control was prepared by PCR with primer 9 (SEQ ID NO: 17) and primer 10 (SEQ ID NO: 18). The gene encoding a novel protein linked to the terminator (amino acid sequence set forth in SEQ ID NO: 2 (ACCESSION No. CCA37552)) was prepared by PCR with primer 11 (SEQ ID NO: 19) and primer 12 (SEQ ID NO: 20).

The secretory signal MFα gene (SEQ ID NO: 21), which was used for vector construction, was prepared by PCR with primer 13 (SEQ ID NO: 22) and primer 14 (SEQ ID NO: 23) using a mixture of chromosomal DNA of *Saccharomyces cerevisiae* strain BY4741 (the nucleotide sequence thereof is described in ACCESSION No. BK006934 to BK006949) as a template.

The Zeocin™ resistance gene under promoter control (SEQ ID NO: 24), which was used for vector construction, was prepared by PCR using synthetic DNA as a template. The G418 resistance gene under promoter control (SEQ ID NO: 25), which was used for vector construction, was prepared by PCR using synthetic DNA as a template.

The anti-lysozyme single-chain antibody (SEQ ID NO: 26), which was used for vector construction, was prepared by PCR using synthetic DNA as a template.

PCR was performed using Prime STAR HS DNA Polymerase (manufactured by Takara Bio Inc.) under reaction conditions according to the method described in the attached manual. The chromosomal DNA was prepared from *Komagataella pastoris* strain ATCC76273 or *Saccharomyces cerevisiae* strain BY4741 using a Kaneka Simple DNA Extraction Kit version 2 (manufactured by Kaneka Corporation), under conditions described therein.

Production Example 2

Construction of Basic Vector

A gene fragment comprising a multi cloning site of HindIII-NotI-BamHI-BglII-XbaI-EcoRI (SEQ ID NO: 27) was fully synthesized, and the fragment was inserted into between HindIII-EcoRI sites of pUC19 (manufactured by Takara Bio Inc., Code No. 3219) to construct pUC-1. A nucleic acid fragment in which EcoRI recognition sequences were added to both ends of the G418 resistance gene under promoter control (SEQ ID NO: 25) was prepared by PCR with primer 15 (SEQ ID NO: 28) and primer 16 (SEQ ID NO: 29), and inserted into the EcoRI site of pUC-1 after treatment with EcoRI to construct pUC_G418.

Then, a nucleic acid fragment of the CCA38473 terminator (SEQ ID NO: 6) was prepared by PCR using primer 7 (SEQ ID NO: 15) and primer 8 (SEQ ID NO: 16), and mixed with nucleic acid fragments of the pUC_G418 treated with XbaI, and joined together using an In-fusion HD Cloning Kit (manufactured by Clontech Laboratories Inc.) to construct pUC_T38473_G418.

Then, a nucleic acid fragment in which a BamHI recognition sequence and a SpeI recognition sequence were added at the ends of the AOX1 promoter (SEQ ID NO: 4) was prepared by PCR with primer 3 (SEQ ID NO: 11) and primer 4 (SEQ ID NO: 12), and a nucleic acid fragment in which a SpeI recognition sequence and a BglII recognition sequence were added at the ends of the secretory signal MFα gene (SEQ NO: 21) was prepared by PCR with primer 13 (SEQ ID NO: 22) and primer 14 (SEQ ID NO: 23). The AOX1 promoter nucleic acid fragment treated with BamHI and SpeI, and the secretory signal MFα gene nucleic acid fragment treated with SpeI and BglII were inserted into between BamHI-BglII sites of pUC_T38473_G418 to construct pUC_Paox1_MFα_T38473_G418.

Next, a nucleic acid fragment in which a MluI recognition sequence and a BglII recognition sequence were added to the ends of the AOX1 terminator (SEQ ID NO: 5) was prepared by PCR with primer 5 (SEQ ID NO: 13) and primer 6 (SEQ ID NO: 14). The fragment was treated with MluI and BglII and then inserted into between the MluI-BglII sites of pUC_Paox1_MFα_T38473_G418 to construct pUC_Paox1_MFα_Taox1_T38473_G418.

Production Example 3

Construction of Anti-Lysozyme Single-Chain Antibody Expression Vector

The anti-lysozyme single-chain antibody gene was prepared by PCR with primer 17 (SEQ ID NO: 30) and primer 18 (SEQ ID NO: 31) using synthetic DNA as a template.

In this nucleic acid fragment, the downstream end region of a secretory signal MFα gene sequence is disposed at the upstream of the nucleotide sequence encoding the anti-lysozyme single-chain antibody as an overlap region, and the upstream end region of an AOX1 terminator sequence is disposed at the downstream thereof as an overlap region. A nucleotide sequence encoding a His tag (SEQ ID NO: 32) is also disposed between the nucleotide sequence encoding the anti-lysozyme single-chain antibody and the upstream end region of the AOX1 terminator sequence.

A nucleic acid fragment was prepared by treating the pUC_Pgap_MFα_Taox1_T38473_G418 constructed in Production Example 2 with XhoI and MluI, and mixed with the nucleic acid fragment of the nucleotide sequence encoding the anti-lysozyme single-chain antibody prepared by the PCR. These fragments were joined together using an In-fusion HD Cloning Kit to construct pUC_Paox1_MFα_scFv_Taox1_T38473_G418. This vector is designed to express the anti-lysozyme single-chain antibody under the control of the AOX1 promoter.

Example 1

Construction of Novel Protein Expression Vector

A nucleic acid fragment in which EcoRI recognition sequences were added to both ends of the Zeocin™ resistance gene under promoter control (SEQ ID NO: 24) was prepared by PCR with primer 19 (SEQ ID NO: 33) and primer 20 (SEQ ID NO: 34), and inserted between EcoRI sites of pUC19 to construct pUC_Zeo.

Next, nucleic acid fragments of the first and second half portions of the ARG4 gene under promoter (SEQ ID NO: 7) control were prepared by PCR with primer 9 (SEQ ID NO: 17) and primer 21 (SEQ ID NO: 35) comprising an AscI-FseI-PmeI restriction enzyme site, and primer 22 (SEQ ID NO: 36) comprising an AscI-FseI-PmeI restriction enzyme site and primer 10 (SEQ ID NO: 18), respectively. These fragments were mixed with pUC_Zeo treated with HindIII and PstI, and joined together using an In-fusion HD Cloning Kit to construct pUC_Arg4_Zeo comprising the Arg4 gene into the middle of which the AscI-FseI-PmeI restriction enzyme site (SEQ ID NO: 37) is inserted.

Then, a nucleic acid fragment in which a SpeI recognition sequence and a XhoI recognition sequence were added to both ends of the EGFP gene (SEQ ID NO: 38) was prepared by PCR with primers 23 (SEQ ID NO: 39) and 24 (SEQ ID NO: 40). The fragment was mixed with pUC_Arg4_Zeo treated with BamHI, and joined together using an In-fusion HD Cloning Kit to construct pUC_Arg4_EGFP_Zeo.

Then, a nucleic acid fragment in which a PstI recognition sequence and a SpeI recognition sequence were added to both ends of the GAP promoter (SEQ ID NO: 3) was prepared by PCR with primer 1 (SEQ ID NO: 9) and primer 2 (SEQ ID NO: 10). The fragment was mixed with pUC_Arg4_EGFP_Zeo treated with SpeI, and joined together using an In-fusion HD Cloning Kit to construct pUC_Arg4_Pgap_EGFP_Zeo.

A nucleic acid fragment in which a XhoI recognition sequence and a HindIII recognition sequence were added to both ends of the AOX1 terminator (SEQ ID NO: 5) was then prepared by PCR with primer 25 (SEQ ID NO: 41) and primer 26 (SEQ ID NO: 42). The fragment was mixed with pUC_Arg4_Pgap_EGFP_Zeo treated with XhoI, and joined together using an In-fusion HD Cloning Kit to construct pUC_Arg4_Pgap_EGFP_Taox1_Zeo.

Then, a nucleic acid fragment in which a SpeI recognition sequence and a HindIII recognition sequence were added to both ends of a gene encoding a novel protein (amino acid sequence set forth in SEQ ID NO: 2 (ACCESSION No. CCA37552)) to which a terminator was linked (SEQ ID NO: 8) was prepared with PCR using primer 11 (SEQ ID NO: 19) and primer 12 (SEQ ID NO: 20). The fragment was mixed with pUC_Arg4_Pgap_EGFP_Taox1_Zeo treated with SpeI and HindIII and joined together using an In-fusion HD Cloning Kit to construct pUC_Arg4_Pgap_CCA37552_T37552_Zeo.

This vector is designed to express the novel protein (amino acid sequence set forth in SEQ ID NO: 2 (ACCESSION No. CCA37552)) under the control of the GAP promoter.

Example 2

Acquisition of Transformed Yeast

The anti-lysozyme single-chain antibody expression vector pUC_Paox1_MRα_scFv_Taox1_T38473_G418 constructed in Production Example 3 was used to transform *Komagataella pastoris*.

A histidine auxotrophic strain derived from *Komagataella pastoris* strain ATCC76273 was cultured in 2 ml of YPD medium (1% dry yeast extract (manufactured by NACALAI TESQUE, INC), 2% Bacto Pepton manufactured by Becton, Dickinson and Company), and 2% glucose) with shaking at 30° C. for 16 hours, then subcultured in fresh YPD medium at 10-fold dilution, and further cultured with shaking at 30° C. for 4 hours. The yeast cells after culture were collected by centrifugation, and washed (6 ml of sterile water was added to suspend the yeast cells, and the yeast cells were collected by centrifugation). The yeast cells were then resuspended with sterile water remaining on the test tube wall, and the resultant suspension was used as a competent cell suspension.

The anti-lysozyme single-chain antibody expression vector pUC_Paox1_MFα_scFv_Taox1_T38473_G418 constructed in Production Example 3 was used to transform E. coli. The obtained transformant was cultured in 5 ml of ampicillin-containing LB medium (1% tryptone (manufactured by NACALAI TESQUE, INC), 0.5% dry yeast extract (manufactured by NACALAI TESQUE, INC.), 1% sodium chloride, and 0.01% sodium ampicillin (manufactured by NACALAI TESQUE, INC.)). From the resulting cells, a plasmid was obtained using a FastGene Plasmid Mini Kit (manufactured by Nippon Genetics Co., Ltd.). The plasmid was linearized by EcoRV treatment using an EcoRV recognition sequence in the CCA38473 terminator.

42 µl of the competent cell suspension and 20 µg of the linearized puC_Paox1_MFα_scFv_Taox1_T38473_G418 were mixed with 8 µl of 10 mg/ml carrier DNA (manufactured by Takara Bio Inc.) solution, 8 µl M DTT solution, 4 µl of 4 M lithium acetate solution, 100 µl of 60% polyethylene glycol solution, and the mixture was allowed to stand still at 42° C. for 20 minutes. After allowing to stand still for 20 minutes, the yeast cells were collected and suspended in 500 µl of YPD medium (1% dry yeast extract (manufactured by NACALAI TESQUE, INC.), 2% Bacto Pepton (manufactured by Becton, Dickinson and Company), and 2% glucose), then allowed to stand still at 30° C. for 2 hours. After allowing to stand still for 2 hours, the yeast cells were applied to a YPDG418 selection agar plate (1% dry yeast extract (manufactured by NACALAI TESQUE, INC.), 2% Bacto Pepton (manufactured by Becton, Dickinson and Company), 2% glucose, 2% agarose, and 0.05% G418 disulfate (manufactured by NACALAI TESQUE, INC.)). A strain that grew in static culture at 30° C. for 3 days was selected, thereby acquiring an anti-lysozyme single-chain antibody expression yeast.

The novel protein expression vector pUC_Arg4_Pgap_CCA37552_T37552_Zeo constructed in Example 1 was used to transform the anti-lysozyme single-chain antibody expression yeast in the same way.

The anti-lysozyme single-chain antibody expression yeast was cultured with shaking in 2 ml of YPD medium (1% dry yeast extract (manufactured by NACALAI TESQUE, INC.), 2% Bacto Pepton (manufactured by Becton, Dickinson and Company), and 2% glucose) at 30° C. for 16 hours, then subcultured in fresh YPD medium at 10-fold dilution, and further cultured with shaking at 30° C. for 4 hours. The yeast cells after culture were collected by centrifugation, and washed (6 ml of sterile water was added to suspend the yeast cells, and the yeast cells were collected by centrifugation). The yeast cells were then resuspended with sterile water remaining on the test tube wall, and the resultant suspension was used as a competent cell suspension.

The novel protein expression vector pUC_Arg4_Pgap_CCA37552_T37552_Zeo constructed in Example 1 was used to transform *E. coli*. The obtained transform was cultured in 5 ml of ampicillin-containing LB medium (1% tryptone (manufactured by NACALAI TESQUE, INC.), 0.5% dry yeast extract (manufactured by NACALAI TESQUE, INC.), 1% sodium chloride, and 0.01% sodium ampicillin (manufactured by NACALAI TESQUE, INC.)). From the resulting cells, a plasmid was obtained using a FastGene Plasmid Mini Kit (manufactured by Nippon Genetics Co., Ltd.). The plasmid was linearized by AscI and PmeI treatment using AscI and PmeI recognition sequences in the ARG4 gene.

42 µl of the competent cell suspension and 20 µg of the linearized pUC_Arg4_Pgap_CCA37552_T37552_Zeo were mixed with 8 µl of 10 mg/ml carrier DNA (manufactured by Takara Bio Inc.) solution, 8 µl of 1 M DTT solution, 4 µl of 4 M lithium acetate solution, and 100 µl of 60% polyethylene glycol solution, and the mixture was allowed to stand still at 42° C. for 20 minutes. After allowing to stand still for 20 minutes, the yeast cells were collected and suspended in 500 µl of YPD medium (1% dry yeast extract (manufactured by NACALAI TESQUE, INC.), 2% Bacto Pepton (manufactured by Becton, Dickinson and Company), and 2% glucose), then allowed to stand still at 30° C. for 2 hours. After allowing to stand still for 2 hours, the yeast cells were applied to YPDG418Zeo selection agar plates (1% dry yeast extract (manufactured by NACALAI TESQUE, INC.), 2% Bacto Pepton (manufactured by Becton, Dickinson and Company), 2% glucose, 2% agarose, 0.05% G418 disulfate (manufactured by NACALAI TESQUE, INC.), and 100 mg/L Zeocin™ (manufactured by InvivoGen)). A strain that grew in static culture at 30° C. for 3 days was selected, thereby an anti-lysozyme single-chain antibody expression yeast in which a gene consisting of the nucleotide sequence set forth in SEQ ID NO: 1 (gene encoding the amino acid sequence set forth in SEQ ID NO: 2) was prepared.

Activation of the gene was confirmed based on the length of amplified nucleic acid fragments by PCR using chromosomal DNA of the transformed yeast as a template, or by analyzing the internal sequences of the fragments, or by conducting a gene expression analysis. As a result, it was confirmed that a gene consisting of the nucleotide sequence set forth in SEQ ID NO: 1 was activated in the transformed yeast prepared in Example 2.

Example 3

Culture of Transformed Yeast

The anti-lysozyme single-chain antibody expression yeast and the anti-lysozyme single-chain antibody expression yeast in which a gene consisting of the nucleotide sequence set forth in SEQ NO: 1 was activated, prepared in Example 2, were inoculated into 2 ml of BMGY medium (1% yeast extract bacto (manufactured by Becton, Dickinson and Company), 2% polypeptone (manufactured by Nihon Pharmaceutical Co., Ltd.), 0.34% yeast nitrogen base without amino acid and ammonitun sulfate (manufactured by Becton, Dickinson and Company), 1% ammonium sulfate, 0.4 mg/l biotin, 100 mM potassium phosphate (pH 6.0), 2% glycerol). The resultant medium was cultured with shaking at 30° C., 170 rpm, for 24 hours to obtain a pre-culture mixture. 200 μl of the pre-culture mixture was subcultured in 2 ml of BMW medium (1% yeast extract bacto (manufactured by Becton, Dickinson and Company), 2% polypeptone (manufactured by Nihon Pharmaceutical Co., Ltd.), 0.34% yeast nitrogen base without amino acid and ammonium sulfate (manufactured by Becton, Dickinson and Company), 1% ammonium sulfate, 0.4 mg/l biotin, 100 mM potassium phosphate (pH 6.0), and 2% methanol), and cultured with shaking at 30° C., 170 rpm, for 72 hours. The culture supernatant was then collected by centrifugation (12000 rpm, 5 minutes, 4° C.).

Example 4

Measurement of Secreted Amount of Anti-Lysozyme Single-Chain Antibody by ELISA Method The expression level of the anti-lysozyme single-chain antibody secreted into the culture supernatant obtained in Example 3 was determined by the Sandwich ELISA (Enzyme-Linked Immunosorbent Assay) method as described below.

A solution of 1 μM/mL lysozyme (manufactured by FUJIFILM Wako Pure Chemical Corporation) dissolved in an immobilized buffer (8 g/L sodium chloride, 0.2 g/L potassium chloride, 1.15 g/L sodium monohydrogen phosphate (anhydrous), 0.2 g/L potassium dihydrogen phosphate (anhydrous), 1 mM magnesium chloride) was added at 50 μl per well in a ELISA plate (Coaster Assay Plate, 96 well Clear, Easywash™ (manufactured by Corning Incorporated)). The plate was incubated at 4° C. overnight. After the incubation, the solution in the well was removed, the well were blocked with 200 μl of Immunoblock (manufactured by Sumitomo Dainippon Pharma Co., Ltd.), and allowed to stand still at room temperature for 1 hour. After washing the well with PBST buffer (8 g/L sodium chloride, 0.2 g/L potassium chloride, 1.15 g/L sodium monohydrogen phosphate (anhydrous), 0.2 g/L potassium dihvdrogen phosphate (anhydrous), 0.1% Tween 20) three times, each of the serially diluted standard anti-lysozyme single-chain antibody and the diluted culture supernatant were added at 50 μl per well, and allowed to react at room temperature for 1 hour. After washing the well with PBST buffer three times, a secondary antibody solution (secondary antibody: Anti-6× His tag antibody (HRP) (manufactured by Abcam plc)) diluted 120,000-fold with PBST buffer was added at 50 μl per well, and allowed to react at room temperature for 1 hour. After washing the well with PBST buffer three times, 50 μl of TMB-1 Component Microwell Peroxidase Substrate SureBlue (manufactured by KPL, Inc.) was added, and the plate was allowed to stand still at room temperature for 3 minutes. After the reaction was stopped by adding 50 μl of TMB Stop Solution (manufactured by Kirkegaard & Perry Laboratories, Inc.), absorbance of 450 nm was measured with a microplate reader (Envison; manufactured by PerkinElmer, Inc.). The quantification of anti-lysozyme single-chain antibodies in the culture supernatant was performed using the calibration curve of standard anti-lysozyme single-chain antibody. The expression level of the secreted anti-lysozyme single-chain antibody determined by this method and the respective cell concentrations (OD660) are shown in Table 2.

As a result, the expression level of the secreted anti-lysozyme single-chain antibody of the strain in which the gene consisting of the nucleotide sequence set forth in SEQ ID NO: 1 had been activated was increased approximately 1.6-fold compared to that of the strain in which the gene had not been activated.

TABLE 2

| ID | Transformed yeast | mg/L | OD 660 |
|---|---|---|---|
| 1 | Anti-lysozyme single-chain antibody expression yeast (Example 2) | 1.98 | 37.8 |
| 2 | Anti-lysozyme single-chain antibody expression yeast in which a gene consisting of the nucleotide sequence set forth in SEQ. ID NO: 1 is activated (Example 2) | 3.09 | 35.1 |

Free Text of Sequence Listing
SEQ ID NO: 3: GAP promoter
SEQ ID NO: 4: AOX1 promoter
SEQ ID NO: 5: AOX1 terminator
SEQ ID NO: 6: CCA38473 terminator
SEQ ID NO: 7: ARG4 gene
SEQ ID NO: 9: Primer 1
SEQ ID NO: 10: Primer 2
SEQ ID NO: H: Primer 3
SEQ ID NO: 12: Primer 4
SEQ ID NO: 13: Primer 5
SEQ ID NO: 14: Primer 6
SEQ ID NO: 15: Primer 7
SEQ ID NO: 16: Primer 8
SEQ ID NO: 17: Primer 9
SEQ ID NO: 18: Primer 10
SEQ ID NO: 19: Primer 11
SEQ ID NO: 20: Primer 12
SEQ ID NO: 22: Primer 13
SEQ ID NO: 23: Primer 14
SEQ ID NO: 24: Zeocin™ resistance gene
SEQ ID NO: 25: G418 resistance gene
SEQ ID NO: 26: svFC gene
SEQ ID NO: 27: HindIII-NotI-BamHI-BglII-XbaI-EcoRI
SEQ ID NO: 28: Primer 15
SEQ ID NO: 29: Primer 16
SEQ ID NO: 30: Primer 17
SEQ ID NO: 31: Primer 18
SEQ ID NO: 32: His tag
SEQ ID NO: 33: Primer 19
SEQ ID NO: 34: Primer 20
SEQ ID NO: 35: Primer 21
SEQ ID NO: 36: Primer 22
SEQ ID NO: 37: AscI-FseI-PmeI
SEQ ID NO: 38: EGFP gene
SEQ ID NO: 39: Primer 23
SEQ ID NO: 40: Primer 24
SEQ ID NO: 41: Primer 25
SEQ ID NO: 42: Primer 26

All the publications, patents, and patent applications cited herein are incorporated herein by citation in their entireties.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

The invention claimed is:

1. A cell, wherein a gene comprising a nucleotide sequence of any one of (a) to (f) is activated:
  (a) the nucleotide sequence set forth in SEQ ID NO: 1;
  (b) the nucleotide sequence of a nucleic acid that hybridizes under a stringent condition to a nucleic acid consisting of a nucleotide sequence complementary to the nucleotide sequence set forth in SEQ ID NO: 1, wherein the stringent condition comprises of a temperature of at least 65° C., a salt concentration of between 0.7 to 1.0 NaCl, and a washing solution comprising sodium chloride and sodium citrate;
  wherein the nucleotide sequence retains the function of the nucleotide sequence of SEQ ID NO: 1, which is an improvement of between more than 1.01 times and less than 100 times in the production amount of a target protein in a cell that has been treated to activate a gene comprising the nucleotide sequence, relative to the production amount of a target protein in a cell that has not been treated to activate the gene comprising the nucleotide sequence;
  (c) the nucleotide sequence having 97% or higher sequence identity to the nucleotide sequence set forth in SEQ ID NO: 1,
  wherein the nucleotide sequence having a sequence identity of 97% or higher to the nucleotide sequence of SEQ ID NO: 1 retains the function of the nucleotide sequence of SEQ ID NO: 1, which is an improvement of between more than 1.01 times and less than 100 times in the production amount of a target protein in a cell that has been treated to activate a gene comprising the nucleotide sequence, relative to the production amount of a target protein in a cell that has not been treated to activate the gene comprising the nucleotide sequence;
  (d) the nucleotide sequence encoding the amino acid sequence set forth in SEQ ID NO: 2;
  (e) the nucleotide sequence encoding an amino acid sequence having 97% or higher sequence identity to the amino acid sequence set forth in SEQ ID NO: 2,
  wherein the amino acid sequence having a sequence identity of 97% or higher to the amino acid sequence of SEQ ID NO: 2 retains the function of the amino acid sequence of SEQ ID NO: 2, which is an improvement of between more than 1.01 times and less than 100 times in the production amount of a target protein in a cell that has been treated to activate a gene comprising the nucleotide sequence encoding the amino acid sequence, relative to the production amount of a target protein in a cell that has not been treated to activate the gene comprising the nucleotide sequence encoding the amino acid sequence;
  (f) a nucleotide sequence encoding an amino acid sequence derived from the amino acid sequence set forth in SEQ ID NO: 2 by substitution, deletion, and/or addition of 1 to up to 15 amino acids,
  wherein the amino acid sequence derived from the amino acid sequence set forth in SEQ ID NO: 2 retains the function of the amino acid sequence of SEQ ID NO: 2, which is an improvement of between more than 1.01 times and less than 100 times in the production amount of a target protein in a cell that has been treated to activate a gene comprising the nucleotide sequence encoding the amino acid sequence, relative to the production amount of a target protein in a cell that has not been treated to activate a gene comprising the nucleotide sequence encoding the amino acid sequence;

wherein the cell comprises a vector comprising:
the nucleotide sequence according to one of (a) to (f).

2. The cell according to claim 1, wherein the cell comprises a vector comprising a nucleotide sequence encoding a target protein.

3. The cell according to claim 1, wherein the cell is a yeast cell, a bacterial cell, a fungal cell, an insect cell, an animal cell, or a plant cell.

4. The cell according to claim 3, wherein the yeast cell is a methanol-utilizing yeast cell, a fission yeast cell, or a budding yeast cell.

5. The cell according to claim 4, wherein the methanol-utilizing yeast cell is a cell of a yeast belonging to the genus *Komagataella* or a cell of a yeast belonging to the genus *Ogataea*.

6. A method for producing a target protein comprising:
culturing the cell according to claim 1, and collecting the target protein from a culture obtained in the culturing step.

7. The method according to claim 6, wherein the target protein is an antibody.

8. A vector comprising a nucleotide sequence of any one of (a) to (f):
(a) the nucleotide sequence set forth in SEQ ID NO: 1;
(b) the nucleotide sequence of a nucleic acid that hybridizes under a stringent condition to a nucleic acid consisting of a nucleotide sequence complementary to the nucleotide sequence set forth in SEQ ID NO: 1, wherein (a) and (b) hybridize under stringent conditions of a temperature of at least 65° C., a salt concentration of between 0.7 to 1.0 N NaCl, and a washing solution comprising sodium chloride and sodium citrate,
wherein the nucleotide sequence retains the function of the nucleotide sequence of SEQ ID NO: 1, which is an improvement of between more than 1.01 times and less than 100 times in the production amount of a target protein in a cell that has been treated to activate a gene comprising the nucleotide sequence, relative to the production amount of a target protein in a cell that has not been treated to activate the gene comprising the nucleotide sequence;
(c) the nucleotide sequence having 97% or higher sequence identity to the nucleotide sequence set forth in SEQ ID NO: 1;
wherein the nucleotide sequence having a sequence identity of 97% or more to the nucleotide sequence of SEQ ID NO: 1 retains the function of the nucleotide sequence of SEQ ID NO: 1, which is an improvement of between more than 1.01 times and less than 100 times in the production amount of a target protein in a cell that has been treated to activate a gene comprising the nucleotide sequence, relative to the production amount of a target protein in a cell that has not been treated to activate the gene comprising the nucleotide sequence;
(d) the nucleotide sequence encoding the amino acid sequence set forth in SEQ ID NO: 2;
(e) the nucleotide sequence encoding an amino acid sequence having 97% or higher sequence identity to the amino acid sequence set forth in SEQ ID NO: 2;
wherein the amino acid sequence having a sequence identity of 97% or higher to the amino acid sequence of SEQ ID NO: 2 retains the function of the nucleotide sequence of SEQ ID NO: 2, which is an improvement of between more than 1.01 times and less than 100 times in the production amount of a target protein in a cell that has been treated to activate a gene comprising the nucleotide sequence encoding the amino acid sequence, relative to the production amount of a target protein in a cell that has not been treated to activate a gene comprising the nucleotide sequence encoding the amino acid sequence;
(f) the nucleotide sequence encoding an amino acid sequence derived from the amino acid sequence set forth in SEQ ID NO: 2 by substitution, deletion, and/or addition of 1 up to 15 amino acids;
wherein the amino acid sequence derived from the amino acid sequence set forth in SEQ ID NO: 2 retains the function of the amino acid sequence of SEQ ID NO: 2, which is an improvement of between more than 1.01 times and less than 100 times in the production amount of a target protein in a cell that has been treated to activate a gene comprising the nucleotide sequence encoding the amino acid sequence, relative to the production amount of a target protein in a cell that has not been treated to activate a gene comprising the nucleotide sequence encoding the amino acid sequence.

* * * * *